United States Patent [19]
Freedman et al.

[11] Patent Number: 6,032,101
[45] Date of Patent: Feb. 29, 2000

[54] METHODS FOR EVALUATING FORMATIONS USING NMR AND OTHER LOGS

[75] Inventors: Robert Freedman, Houston; Chanh Cao Minh, Katy, both of Tex.

[73] Assignee: Schlumberger Technology Corporation, Houston, Tex.

[21] Appl. No.: 09/056,909

[22] Filed: Apr. 8, 1998

Related U.S. Application Data

[63] Continuation-in-part of application No. 08/873,981, Jun. 12, 1997
[60] Provisional application No. 60/042,059, Apr. 9, 1997.
[51] Int. Cl.[7] .................................................. G06F 19/00
[52] U.S. Cl. ................................................ 702/8; 702/8
[58] Field of Search .................................. 702/6, 7, 8, 13; 324/303, 324; 73/152.08, 152.06, 152.05

[56] References Cited

PUBLICATIONS

M.H. Waxman and L.J.M. Smits, "Electrical Conductivities in Oil–Bearing Shaly Sands," *Soc. Pet. Eng. J.* (Jun. 1968), presented as Paper SPE 1863–A at SPE 42$^{nd}$ Annual Fall Meeting, Houston, Texas (Oct. 1 –4, 1967).

C. Clavier, G. Coates and J. Dumanoir, "The Theoretical and Experimental Bases for the 'Dual Water 'Model for the Interpretation of Shaly Sands," 6859 *Society of Petroleum Engineers Transactions*, pp. v5 –v20 (1977).

R. Freedman, A. Boyd, G. Gubelin, D. McKeon, C.E. Morriss, and C. Flaum "Measurement of Total NMR Porosity Adds New Value to NMR Logging," Paper O, *Transactions of the Soc. of Prof. Well Log Analysts 38$^{th}$ Annual Logging Symposium* (1997).

R. Akkurt, H.J. Vinegar, P.N. Tutunjian and A.J. Guillory, "NMR Logging of Natural Gas Reservoirs," Paper N, Transactions of the Society of Professional Well Log Analysts 36$^{th}$ Annual Logging Symposium (1995).

M.G. Prammer, E.D. Drack, J.C. Bouton and J.S. Gardner, "Measurements of Clay–Bound Water and Total Porosity by Magnetic Resonance Logging," SPE paper 35622, presented at Society of Petroleum Engineers Annual Technical Conference and Exhibition (1996).

C. Flaum, R.L. Kleinberg and M.D. Hurlimann, "Identification of Gas with the Combinable Magnetic Resonance Tool," Transactions of the Society of Professional Well Log Analysts 37$^{th}$ Annual Logging Symposium (1996).

*Primary Examiner*—Donald E. McElheny, Jr.
*Attorney, Agent, or Firm*—John Ryberg; Brigitte L. Jeffery

[57] ABSTRACT

Methods that allow in-situ calculations of critical petrophysical parameters including, but not limited to, $\phi_t$, $S_{xot}$, $Q_v$, F, and $R_w$ are provided. Also, NMR clay bound water may be used to estimate a continuous $Q_v$. In combination with other resistivity logs, such as SP, $R_{xo}$ and $R_{deep}$, $R_w$ can be determined. With the exception of the saturation exponent n, all Archie parameters and other computational equivalents are continuously determined directly from well logs. The methods therefore allow $S_w$ to be determined more accurately, which leads to improved estimation of hydrocarbon reserves. The method is extended to complex lithology with additional tools. In complex lithology, permeability estimation is also improved using a method that estimates bound fluid volume. Also, an uncertainty analysis of the gas-corrected parameters is also provided.

47 Claims, 4 Drawing Sheets

METHODS FOR EVALUATING FORMATIONS USING NMR AND OTHER LOGS

CROSS REFERENCE TO RELATED APPLICATIONS

This is a continuation-in-part of copending U.S. patent application Ser. No. 08/873,981, filed Jun. 12, 1997, which claims the benefit of U.S. provisional application No. 60/042,059, filed Apr. 9, 1997.

FIELD OF THE INVENTION

This invention relates to methods for evaluating a subsurface formation. More particularly, this invention relates to methods for determining parameters that characterize a formation using nuclear magnetic resonance ("NMR") logging data, especially in combination with other types of logging data.

BACKGROUND OF THE INVENTION

The economic value of a formation containing hydrocarbons depends on the amount of oil or gas contained in a unit volume of a subsurface reservoir, which, among other things, is a function of its porosity and its hydrocarbon saturation. Total porosity $\phi_t$ of a formation is the fraction of the formation per unit volume occupied by pore spaces. Hydrocarbon saturation $S_h$ is a fraction of the pore volume filled with hydrocarbons. In addition to porosity $\phi_t$ and hydrocarbon saturation $S_h$, permeability k of a formation indicates the ease with which a fluid (e.g., hydrocarbons) flows through, and can be removed from, the formation. Although a large porosity usually corresponds to a large permeability, pore size, shape, and continuity also influence permeability.

There are many well-known models that allow the calculation of saturation from well logs. In shaly formations, the preferred models are the Waxman-Smits model (See, e.g., M. H. Waxman and L. J. M. Smits, "Electrical Conductivities in Oil-Bearing Shaly Sands," *Society of Petroleum Engineers 42nd Annual Fall Meeting*, (Oct. 1–4, 1967), and the Dual Water model (See e.g., C. Clavier, G. Coates, and J. Dumanoir, "The Theoretical and Experimental Bases for the 'Dual Water' Model for the Interpretation of Shaly Sands," *Society of Petroleum Engineers Transactions* 6859 (1977) (hereinafter, "Clavier et al."). Both models rely on the cation exchange capacity per unit volume $Q_v$ and the formation factor F, which are not often measured downhole nor inferred directly from logging measurements.

NMR is based on the fact that the nuclei of many elements have angular momentum (hereinafter, "spin") and a magnetic moment. Nuclear spins align themselves along an externally applied static magnetic field and obtain an equilibrium condition. This equilibrium can be disturbed by a pulse of an oscillating magnetic field, which tips the spins away from the static field direction. The degree to which the spins are tipped is under the control of the experimenter as explained below.

After tipping, two things occur simultaneously. First, the spins precess around the static field at the Larmor frequency ($\omega_o = \gamma B_0$), where $B_0$ is the strength of the static field and $\gamma$ is the gyromagnetic ratio, a nuclear constant. Second, the spins return to the equilibrium condition according to a decay time known as the "spin-lattice relaxation time" or $T_1$. $T_1$ is controlled by the molecular environment and is typically ten to one thousand milliseconds for water in rocks.

Also associated with the spin of molecular nuclei is a second relaxation time known as "spin-spin relaxation time" or $T_2$. At the end of a ninety degree tipping pulse, all the spins point in a common direction perpendicular to the static field, and they precess at the Larmor frequency. However, small inhomogeneities in the static field due to imperfect instrumentation or microscopic material heterogeneities cause each of the nuclear spins to precess at a slightly different rate. Therefore, after some time, the spins will not precess in unison, that is they will dephase. When dephasing is due to static field inhomogeneity of the apparatus, the dephasing time is called $T_2^*$. When the dephasing is due to properties of the material, the dephasing time is called $T_2$.

$T_2$ can be several seconds in an unconfined low viscosity liquid such as water, and as short as ten microseconds in a solid. Liquids confined in the pores of rocks present an intermediate case where $T_2$ is in the range of tens to hundreds of milliseconds, depending on various factors, such as pore size and fluid viscosity.

A known method for measuring $T_2$ is called the Carr-Purcell-Meiboom-Gill ("CPMG") sequencing method. In solids, where $T_2$ is very short, $T_2$ can be determined from the decay of a detected signal after a ninety degree pulse. However, for liquids where $T_2^* \ll T_2$, the free induction decay becomes a measurement of the apparatus-induced inhomogeneities. To measure the true $T_2$ in such liquids, it is necessary to cancel the effect of the apparatus-induced inhomogeneities.

This cancellation is achieved by applying a sequence of pulses. The first pulse is a ninety degree pulse that causes the spins to start precessing. After the spins have begun precessing, a one hundred eighty degree pulse is applied to keep the spins in the measurement plane, but to cause the spins which are dispersing in the transverse plane to precess in the reverse direction, thereby refocusing the spins. By repeatedly reversing and refocusing the spins by one hundred eighty degree pulses, a series of "spin echoes" occur. This succession of one hundred eighty degree pulses, after the initial ninety degree pulse, is the Carr-Purcell sequence which measures the irreversible dephasing (i.e., $T_2$) due to material properties. Meiboom and Gill devised a modification to the Carr-Purcell pulse sequence such that, after the spins are tipped by ninety degrees and start to dephase, the carrier of the one hundred eighty degree pulses relative to the carrier of the ninety degree pulse. As a result, any error that occurs during an even pulse of the CPMG sequence is canceled out by an opposing error in the odd pulse. A detailed explanation of NMR principles and pulse sequences is described in Freedman U.S. Pat. No. 5,291,137.

Unfortunately, the presence of gas in rock pores adversely effects the derivation of total formation porosity $\phi_t$. See, e.g., Robert Freedman, Austin Boyd, Greg Gubelin, Donald McKeon, and Chris Morriss, "Measurement of Total NMR Porosity Adds New Value to NMR Logging," Paper O, *Transactions of the Society of Professional Well Log Analysts* 38th *Annual Logging Symposium* (1997).

For example, NMR-derived total porosities $\phi_{nmr}$ are generally underestimated when gas is present in the zone being measured. At least two effects may be responsible for the underestimation of $\phi_t$. The first effect is related to an abnormally low hydrogen index of gas. The low index effect is familiar to log analysts because it also causes neutron tool porosities to be reduced in gas zones. The second effect is related to insufficient polarization of the gas. The insufficient polarization effect occurs because reservoir gas has longitudinal relaxation times $T_1$ that are in the range from between 3 and 6 seconds at normal reservoir conditions. Because $T_1$ is so long, the time required to fully polarize reservoir gas is on the order of ten seconds using conventional pulse sequences, such as the Carr-Purcell-Meiboom-Gill ("CPMG") sequences. Unfortunately, a ten second wait time is generally impractical for routine logging operations because it results in very slow logging speeds.

Many previously published methods for using NMR data to detect and quantify hydrocarbons in formations are "NMR-only" methods. That is, these methods use NMR data alone to derive hydrocarbon-related and porosity-related parameters. Most of these methods are based on concepts introduced by Akkurt et al., who recognized that the differences between the NMR properties of water and non-wetting hydrocarbons in porous rocks provides a means for distinguishing formation fluids into gas, oil, and water volumes. R. Akkurt, H. J. Vinegar, P. N. Tutunjian, and A. J. Guillory, "NMR logging of natural gas reservoirs," Paper N, *Transactions of the Society of Professional Well Log Analysts 36th Annual Logging Symposium* (1995).

In the same paper, Akkurt et al. introduced a detailed method for identifying and typing hydrocarbons. That method is called the Differential Spectrum Method (hereinafter, "DSM"). Later, an improvement to the DSM method, known as Time Domain Analysis (hereinafter, "TDA"), was developed by M. G. Prammer, E. D. Drack, J. C. Bouton, J. S. Gardner, G. R. Coates, R. N. Chandler, and M. N. Miller, "Measurements of clay-bound water and total porosity by magnetic resonance logging," SPE Paper 35622, presented at the *Society of Petroleum Engineers Annual Technical Conference and Exhibition* (1996).

The DSM and TDA methods were both developed for use with tools having a fixed magnetic field gradient (such as the tool available under the trademark MRIL®, by Numar Corporation, of Malvern, Pa.). More recently, another NMR-only method of detecting gas, known as the Echo Ratio Method (hereinafter, "ERM"), was developed by Flaum et al. C. Flaum, R. L. Kleinberg, M. D. Hürlimann, "Identification of gas with the Combinable Magnetic Resonance tool (CMR*)," Paper L, *Transactions of the Society of Professional Well Log Analysts 37th Annual Logging Symposium* (1996). ERM uses a CMR tool which has a saddle point distribution of magnetic field gradients. ERM identifies gas using apparent diffusion constants computed from the ratios of two $T_2$-decay curves acquired with different echo spacings.

These NMR-only methods for calculating porosity and other parameters have various disadvantages. First, these methods work best with a tool that has a fixed or saddle point distribution of magnetic field gradients. Thus, these methods are limited by the type of NMR tool used to acquire data. Second, the NMR-only methods (e.g., ERM) may require data from two NMR measurements having different CPMG sequences. Third, the NMR-only methods require that the gas be appreciably polarized, which means long wait times and slow logging speeds. And fourth, total porosity derivations from NMR-only techniques tend to be computationally complex.

The presence of gas also adversely effects the calculation of density-derived total porosity $\phi_{density}$. Unlike NMR-derived total porosity $\phi_{nmr}$, which underestimates true total porosity, density-derived total porosity overestimates true total porosity when gas is present in the formation. Thus, in a gas bearing zone, $\phi_{nmr}$ will be less than $\phi_{density}$ and the difference between the two porosity logs will be proportional to the gas saturation in the zones. The difference effect is analogous to the "neutron-density" crossover effect in gas zones. The same effect can occur when there is gas condensate or light oil in the formation. However, the magnitude of the effect is reduced. The use of neutron-density logs for gas detection is not reliable because the effects of shale and thermal neutron absorbers on the neutron-density log response can totally suppress the crossover effect. Also, neutron-density-derived total porosities can be inaccurate because of mineralogy effects on the neutron tool response.

Furthermore, conventional calculation of water saturation in shaly formations require knowledge of the formation factor F and cation exchange capacity per unit volume $Q_v$. Obtaining this knowledge requires core sample measurements. Such core sample measurements, however, are inconvenient, time-consuming, and costly because they require that core samples be brought to the surface and analyzed, usually at an off-site laboratory. And, the cost generally scales with the number of core samples analyzed, which at times can be very large. Therefore, immediate on-site valuation of $Q_v$ and F are precluded using conventional evaluation techniques.

In view of the foregoing, it is an object of this invention to provide methods for accurately determining gas-corrected flushed zone and virgin zone parameters that characterize zones in a formation, even a shaly or gas bearing formation.

It is also an object of this invention to provide methods that allow immediate on-site valuation of formations, without performing uphole core sample analysis.

It is also an object of this invention to provide methods that accurately determine such parameters using nearly any conventional NMR tool, including fixed gradient tools and saddle point tools that have a distribution of magnetic field gradients.

It is yet another object of this invention to provide methods for determining gas-corrected total porosity and flushed zone gas saturation by combining NMR and density log measurements.

It is yet a further object of this invention to combine NMR measurements with other open hole logs to determine critical petrophysical parameters, such as virgin formation hydrocarbon saturation and permeability, needed in the estimation of hydrocarbon reserves and producibility.

It is yet an additional object of this invention to estimate the uncertainty of the magnitudes of the petrophysical parameters determined in accordance with this invention.

SUMMARY OF THE INVENTION

These and other objects of the invention are accomplished in accordance with the principles of the invention by providing methods that allow in-situ estimations of critical petrophysical parameters including, but not limited to $Q_v$, F, and $R_w$, even in the difficult case of shaly and gas bearing formations. The method can also be used to provide permeability and producibility answers.

Furthermore, NMR clay bound water may be used to estimate a continuous $Q_v$. With other resistivity logs such as SP, $R_{xo}$, $R_{deep}$, continuous F and $R_w$ can be determined. With the exception of the saturation exponent n, all Archie parameters are continuously determined directly from well logs, including any computational equivalents of these parameters. As used herein, a computational equivalent is any parameter immediately derivable from a parameter that has been determined according to this invention. The method thus allows $S_w$ to be determined more accurately, which leads to improved estimation of hydrocarbon reserves. The methodology is extended to complex lithology with additional tools.

In accordance with this invention, a method for characterizing a gas-bearing formation traversed by a borehole is provided. The method includes (1) computing an NMR-derived total porosity $\phi_{nmr}$ and a density-derived total porosity $\phi_{density}$, (2) determining a gas-corrected total porosity $\phi_t$ using the $\phi_{nmr}$ and the $\phi_{density}$, (3) determining a gas-corrected total water saturation $S_{xot}$ in the flushed zone using the $\phi_{nmr}$ and the $\phi_{density}$, and (4) determining resistivity parameters, $X_{mf}$ and m, using Archie's equation extended for shaly formations:

$$C_{xo} = S_{xot}^n \varnothing_t^m \left( C_{mf} + \frac{X_{mf}}{S_{xot}} \right), \qquad (1)$$

n is a saturation exponent, m is a model-dependent cementation exponent, $C_{xo}$ is a conductivity in the flushed zone, $C_{xo}$ being equal to $1/R_{xo}$, where $R_{xo}$ is a flushed zone resistivity, $C_{mf}$ is a mud filtrate conductivity, $C_{mf}$ being equal to $1/R_{mf}$, where $R_{mf}$ is a resistivity of the mud filtrate, and where $X_{mf}$ is a model-dependent clay conductivity. The parameters that appear in Equation (1) are sometimes referred to as Archie parameters. $\phi_t$, $X_{mf}$, and m are then used in conjunction with a true resistivity $R_{true}$ to compute a water saturation $S_{wt}$ in the virgin zone according to:

$$C_{true} = S_{wt}^n \varnothing_t^m \left( C_w + \frac{X_w}{S_{wt}} \right) \qquad (2)$$

with $C_{true}=1/R_{true}$, where $R_{true}$ is the virgin zone resistivity, and $C_w=1/R_w$, where $R_w$ is the water resistivity.

In accordance with another aspect of this invention, a method for characterizing a formation traversed by a borehole using NMR data without density data is also provided. The method includes in a first step receiving NMR data characterizing the flushed zone. The NMR data preferably includes a $T_2$ distribution $P(T_2)$. Then, in a second step, clay bound water volume Vbound is determined substantially according to:

$$V_b = \int_{T_2 \min}^{T_2 \max} P(T_2) d T_2, \qquad (3)$$

where $T_2$min is a minimum $T_2$ for clay bound water and $T_2$max is a maximum $T_2$ for clay bound water. And, in a third step, a cation exchange capacity per unit total pore volume $Q_v$ is determined using a clay bound water saturation $S_{wb}$ model.

In yet another aspect of this invention, a method for characterizing a formation traversed by a borehole using the spontaneous potential is provided. The method includes receiving SP logging data and using that data to determine $R_w$ or a cation exchange capacity per unit total pore volume $Q_v$ with an electrochemical potential model, such as the one detailed in L. J. M. Smits, "SP Log Interpretation in Shaly Sands," *Society of Petroleum Engineers Journal*, vol. 8, pp. 123–136 (1968). Preferably, the method involves at least a two step process. First, the Laplace Equation $\nabla \sigma_c \cdot \nabla V = 0$ is solved to determine the SP source, where $\sigma_c$ is a conductivity and V is a potential everywhere in the formation. Next, the SP source integral Equation (33) is solved for $R_w$ or $Q_v$.

And, according to yet a further aspect of the invention, a method for determining the bound fluid volume BFV of a formation with complex lithology traversed by a borehole is provided. The method includes receiving NMR data characterizing a flushed zone of the formation and determining the bound fluid volume BFV of the formation by summing the $BFV_i$ constituents weighted by their respective constituent volumes $V_i$, where i is an index denoting different constituents.

Furthermore, according to an additional aspect of this invention, a method for analyzing the uncertainty of certain resistivity parameters is provided. The method includes calculating the variance of a gas-corrected petrophysical parameter substantially according to:

$$\sigma^2(f) \cong \sum_{i=1}^{n} \left( \frac{\partial f}{\partial x_i} \right)_{x_i^*}^2 \sigma^2(x_i), \qquad (4)$$

where $f$ is a parameter that is a function of n variables $x_n$, $\sigma^2(f)$ is a variance of $f$, and $x_i^*$ is a best estimate for each of the n variables.

Further features of the invention, its nature and various advantages will be more apparent from the accompanying drawings and the following detailed description of the preferred embodiments.

DETAILED DESCRIPTION OF THE INVENTION

Figure 1:
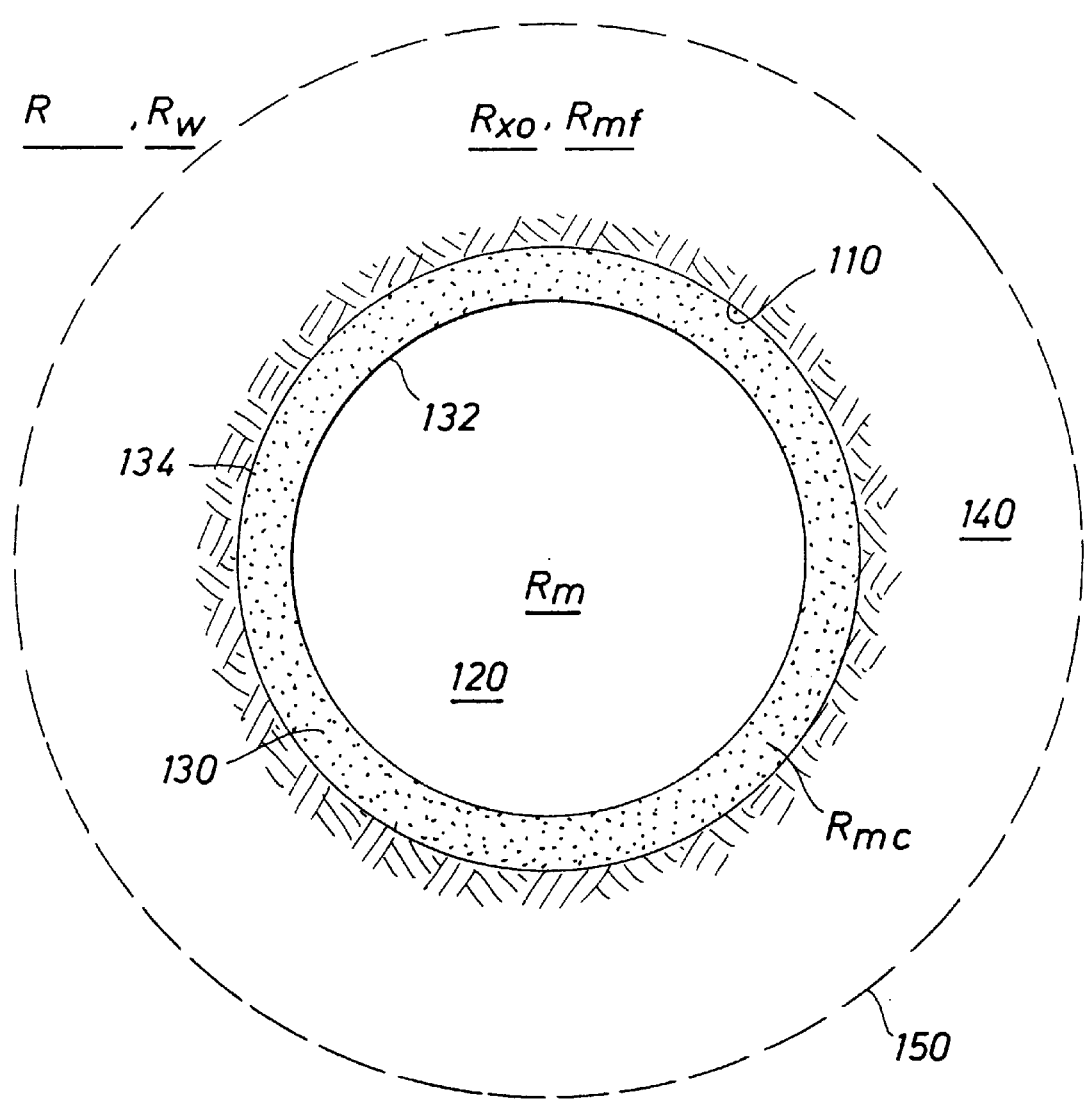
FIG. 1 shows a simplified schematic representation of a horizontal cross-section of a permeable formation.

FIG. 1 is a simplified schematic representation of a horizontal cross-section of a permeable formation 100 in which a borehole has been drilled. During drilling, the hydrostatic pressure of mud column 120 in borehole 110 is usually greater than the pore pressure of formation 100. The resistivity of the mud in the borehole is called mud resistivity $R_m$. The pressure differential between mud column 120 and formation 100 forces the mud-filtrate that makes mud column 120 into formation 100, and the solid particles of the mud are deposited on the borehole wall after they form mudcake 130, which has resistivity $R_{mc}$. Inner diameter 132 of mudcake 130 is normally measured with calipers and thus is sometimes referred to as "Cali." Outer diameter 134 is determined by the outer diameter of the bit used to drill the borehole.

In the radial zone close to borehole 110, most of the original formation water and some hydrocarbons may be flushed away by the filtrate. This zone is referred to as flushed (or invaded) zone 140, which has resistivity $R_{xo}$. The resistivity of the mud filtrate in flushed zone 140 is called mud filtrate resistivity $R_{mf}$. Outer diameter 150 of flushed zone 140 is sometimes referred to as "Di."

Beyond flushed zone 140, the displacement of the formation fluids by the mud filtrate is less complete. The radial extent of flushed zone 140 depends on many factors including the type of drilling mud, the formation porosity, the formation permeability, the pressure differential, and the time since the formation was first drilled. The undisturbed formation beyond the flushed zone is referred to as uncontaminated or virgin zone 160, which has true resistivity $R_{true}$. The water in virgin zone 160 has resistivity $R_w$.

The electrical resistivity of a substance is its ability to impede the flow of electrical current through the substance. Electrical conductivity is the reciprocal of resistivity. Resistivity measurements have been employed, singly and in combination, to determine $R_{true}$ in virgin zone 160. They are also used to determine $R_{xo}$.

The resistivity of clean, water-bearing formations (i.e., one containing no appreciable amount of clay and no hydrocarbons) is proportional to the resistivity $R_w$ of brine when saturated. The constant of proportionality is called the formation resistivity factor, F. Archie proposed a formula relating porosity $\phi$ to the formation factor F (F=$\alpha \div \phi^m$), where $\alpha$ is a proportionality factor and m is a cementation exponent (see G. E. Archie, "The Electrical Resistivity as an Aid in Determining Some Reservoir Characteristics," *J. Pet. Tech.*, Vol. 5, No. 1, (January 1942) and G. E. Archie, "Classification of Carbonate Reservoir Rocks and Petrophysical considerations," *Bull., AAPG*, Vol 36, No. 2, (February 1952)).

Assuming that the rocks in the formation are perfect insulators when dry, the resistivity of a formation containing oil or gas and water is, among other things, a function of F, $R_w$, and $S_w$, where $S_w$ is the fraction of the pore volume occupied by formation water. From Archie's equation, water saturation $S_w$ of a clean formation can be expressed in terms of its true resistivity $R_{true}$ as:

$$S_w^n = \frac{FR_w}{R_{true}}, \quad (5)$$

where n is a saturation exponent, which is usually approximated as 2. Water (mud filtrate) saturation $S_{xo}$ of flushed zone 140 can also be expressed in a similar fashion as:

$$S_{xo}^n = \frac{FR_{mf}}{R_{x0}}, \quad (6)$$

$S_{xo}$ of flushed zone 140 is equal to $1-S_{hr}$, where $S_{hr}$ is the residual hydrocarbon saturation in flushed zone 140.

Some rocks in the formation, such as clays and shales, are not perfect insulators when dry. For example, clays and shales have substantial conductivities. Formations that are substantially shaly are usually referred to as shaly formations, and are often considered difficult formations to evaluate using conventional logging techniques. Because all logging measurements are influenced by the presence of shale, corrections for shale content are required for an accurate picture of the formation.

In accordance with this invention, at least three methods for characterizing gas-bearing formations using NMR data, density data, and electrical data are provided. In a first method, $Q_v$ is computed from an NMR tool measurement (see FIG. 2). In a second method, $Q_v$ is computed from a shallow electrical tool measurement (see FIG. 3). And, in a third method, $Q_v$ is computed from a spontaneous potential measurement SP (see FIG. 4).

Figure 2:
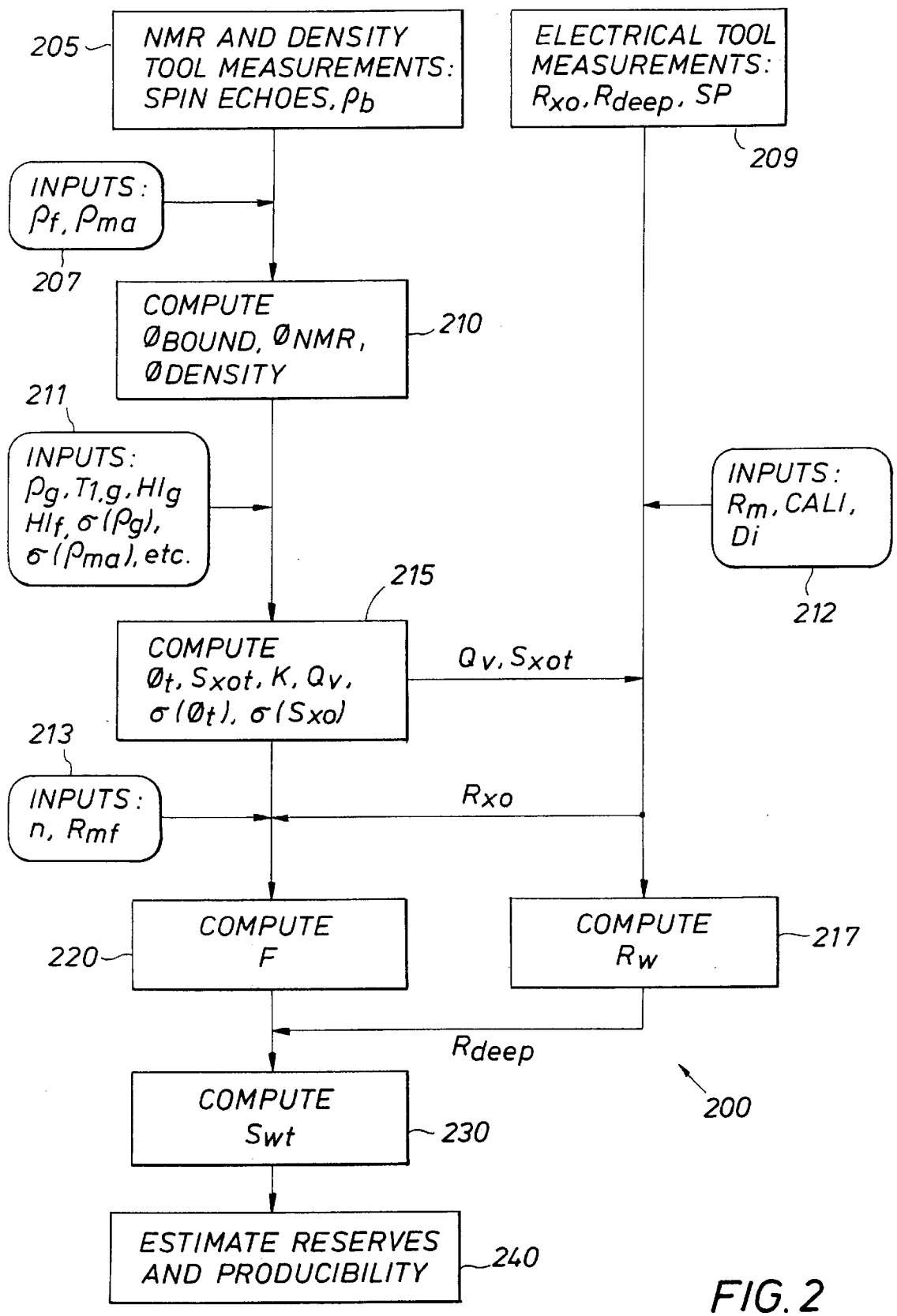
FIG. 2 is a flow chart of steps for carrying out a first illustrative embodiment of the method for characterizing a gas-bearing formation traversed by a borehole.

FIG. 2 shows first method 200 for characterizing a formation according to this invention. Method 200 at least includes, in step 210, computing at least $\phi_{nmr}$, $\phi_{density}$, and $\phi_{bound}$ of a flushed zone; in step 215, computing at least $\phi_t$ and $S_{xot}$ using $\phi_{nmr}$ and $\phi_{density}$ in the flushed zone; in step 220, computing a formation factor F; in step 209, making electrical tool measurements; in step 217, computing $R_w$; in step 230, computing $S_{wt}$; and in step 240, estimating reserves and producibility of the formation. The method involves determining $X_{mf}$ and m using:

$$C_{xo} = S_{xot}^n \varnothing_t^m \left( C_{mf} + \frac{X_{mf}}{S_{xot}} \right), \quad (7)$$

where n is a saturation exponent, m is a model-dependent cementation exponent, $C_{xo}$ is a conductivity in the flushed zone, $C_{xo}$ being equal to $1/R_{xo}$, where $R_{xo}$ is a flushed zone resistivity, $C_{mf}$ is a mud filtrate conductivity, $C_{mf}$ being equal to $1/R_{mf}$, where $R_{mf}$ is a resistivity of the mud filtrate, and where $X_{mf}$ is a model-dependent clay conductivity. Equation (7) is sometimes referred to as Archie's equation as extended to shaly formations. It is understood that each of the variables above may correspond to one point in the flushed zone of the formation (e.g., a single depth) or to a set of points (e.g., a depth profile) in the flushed zone of the formation.

Before $\phi_{nmr}$ is computed in step 210, NMR data that characterizes the formation can be measured, as shown in step 205. In step 205, a first portion of the earth formation is measured with a nuclear magnetic resonance tool. This preferably involves measuring a first portion of the earth formation with a down-hole nuclear magnetic resonance tool to obtain NMR data. Any type of down-hole NMR-logging tool can be used (such as, for example, the tools sold under the trademark CMR®, by Schlumberger Technology Corporation, of Houston, Tex. or under the trademark MRIL®, by Numar Corporation, of Malvern, Pa.).

Once $\phi_{nmr}$ is computed, it is preferably stored in a memory unit. The memory unit may be downhole or uphole. Alternatively, $\phi_{nmr}$ may be transmitted directly to a processor for use in determining $\phi_t$ and $S_{xot}$ in step 215.

$\phi_{density}$ is preferably computed from density data that characterizes the formation. Therefore, in step 205, a second portion of the earth formation is also measured with a density tool, preferably with a down-hole density tool. Any type of down-hole density tool can be used, including a high-energy gamma-gamma radiation tool.

Preferably, the first and second portions measured in step 205 are substantially the same. This means that, at a particular longitudinal (e.g., vertical) position along the borehole, the radial (e.g., lateral) depths of evaluation of the NMR and density tools are well matched. An example of a well matched pair of tools is a CMR tool and a high energy gamma-gamma radiation tool. See D. V. Ellis, *Well Logging for Earth Scientists* (1987). Thus, in accordance with the principles of this invention, it is assumed that shallow-reading tools, such as NMR, Density, $R_{xo}$, and EPT logging tools, evaluate substantially the same longitudinal and radial location of flushed zone 140. Moreover, in order to obtain virgin zone parameters in step 230, it is further assumed that $\phi_t$ and F are substantially laterally invariant.

$\phi_{density}$ may be computed in step 210 from the density data measured in step 205 using any conventional calculation method. Once computed, $\phi_{density}$ may be stored in a memory unit. This memory unit may be the same memory unit used to store $\phi_{nmr}$, or a different memory unit, and may be located downhole or uphole. Like $\phi_{nmr}$, $\phi_{density}$ may be transmitted directly to a processor for use in determining $\phi_t$ and $S_{xot}$ in step 215 without being stored.

In step 215, the gas-corrected total porosity $\phi_t$ may be determined substantially according to:

$$\phi_t = \frac{\phi_{density}\left(1 - \frac{(HI)_g P_g}{(HI)_f}\right) + \phi_{nmr}\left(\frac{\lambda}{(HI)_f}\right)}{\left(1 - \frac{(HI)_g P_g}{(HI)_f}\right) + \lambda}, \quad (8)$$

where $(HI)_g$ is the Hydrogen Index of the gas, $(HI)_f$ is the Hydrogen Index of the liquid phase consisting of a mixture of mud filtrate and formation water, $P_g$ is the gas polarization function, which is defined as $1-\exp(-WT/T_{l,gas})$, where WT is the wait time for a pulse sequence and $T_{l,gas}$ is a gas longitudinal relaxation time (See R. Freedman, "Gas Corrected Porosity from Density Porosity and CMR Measurements in 'How to Use Borehole NMR,'" *Oilfield Review*, vol. 9, No. 2, pp. 54) (hereinafter, "Freedman"). $\lambda$ is proportional to the density difference between the gas and liquid phases and is responsible for the gas effect on $\phi_{density}$. $\lambda$ may be determined substantially according to:

$$\lambda = \frac{\rho_f - \rho_g}{\rho_{ma} - \rho_f} \quad (9)$$

where $\rho_f$ is the density of the liquid phase, $\rho_{ma}$ is the formation matrix density, and $\rho_g$ is the density of the gas. Computation of $\phi_{density}$ in step 210 requires at least two inputs, including $\rho_{ma}$ and $\rho_f$. $\phi_{density}$ may be determined according to:

$$\phi_{density} = \frac{\rho_b - \rho_{ma}}{\rho_f - \rho_{ma}}, \quad (10)$$

where $\rho_b$ is the formation bulk density $\rho_b$.

It should be understood by a person of ordinary skill in the art that the computation of $\phi_t$ and $S_{xot}$ can be performed individually through a series of intermediate steps, or by calculating any computationally equivalent parameter. Computation of $\phi_t$ and $S_{xot}$ in step 215 requires several inputs, including, for example, $\rho_g$, $T_{l,gas}$, $(HI)_g$, $(HI)_f$, $\rho_f$, and $\rho_{ma}$, as shown in step 211.

When the formation is lithologically simple (i.e., the formation only includes one principal type of rock), determination of the matrix density $\rho_{ma}$ and other density-derived parameters, is straightforward because the value of $\rho_{ma}$ is usually well-known. However, when a formation includes two or more principal constituents (such as sandstone and limestone), $\rho_{ma}$ may be determined, in step 207, substantially according to:

$$\rho_{ma} = \frac{\sum_i V_i \rho_i}{\sum_i V_i}, \quad (11)$$

where $V_i$ is the volume and $\rho_i$ is the density of a formation constituent i. $V_i$ may be determined using one or more logging techniques. $\rho_i$ values for most constituents are generally known to a person of ordinary skill in the art. For example, the density of a formation of limestone $\rho_{limestone}$ is known to be about 2.71 g/cc and the density of a formation of sandstone $\rho_{sandstone}$ is about 2.65 g/cc. Some of the techniques that may be used to obtain $V_i$ include Thorium logging, Potassium logging, Neutron logging, Sonic logging, Photoelectric logging, Elemental Yield logging, and any combination thereof.

In step 215, $\phi_t$ may be determined from Equation (8) substantially according to:

$$\phi_t = \phi_{density} * w + (1-w) * \frac{\phi_{nmr}}{(HI)_f}, \quad (12)$$

where the w is determined substantially according to:

$$w = \frac{1 - \frac{(HI)_g * P_g}{(HI)_f}}{\left(1 - \frac{(HI)_g * P_g}{(HI)_f}\right) + \lambda}, \quad (13)$$

where $(HI)_g$, $(HI)_f$, $P_g$, and $\lambda$ are defined above. Therefore, when the formation has a complex lithology, a more accurate determination of w can be achieved by determining $\rho_{ma}$ according to Equation (11).

Generally, in a gas reservoir, w has a value between about 0.55 and about 0.65, and thus $\phi_t$ can be estimated using a value in that range. $\phi_t$ is preferably estimated by setting w equal to about 0.60. Thus, Equation (12) reduces to:

$$\phi_t = (0.60)\phi_{density} + \frac{(0.40)}{(HI)_f}\phi_{nmr}. \quad (14)$$

In addition to determining $\phi_t$ in step 215, the gas-corrected total water saturation $S_{xot}$ in the flushed zone, or a computational equivalent, is computed. Preferably, $S_{xot}$ is determined substantially according to: $S_{xot}=V_{xot}/\phi_t$, where $V_{xot}$ is the total water volume of the flushed zone. $V_{xot}$ may be determined substantially according to: $V_{xot}=\phi_t-V_{g,xo}$, where $V_{g,xo}$ is the gas volume of the flushed zone. $V_{g,xo}$ and $S_{g,xo}$ may be determined substantially according to (See, Freedman):

$$V_{g,xo} = \frac{\phi_{density} - \frac{\phi_{nmr}}{(HI)_f}}{\left(1 - \frac{(HI)_g P_g}{(HI)_f}\right) + \lambda}, \text{ and} \quad (15)$$

$$S_{g,xo} = \frac{\phi_{density} - \frac{\phi_{nmr}}{(HI)_f}}{\phi_{density} * \left(1 - \frac{(HI)_g * P_g}{(HI)_f}\right) + \frac{\lambda * \phi_{nmr}}{(HI)_f}}. \quad (16)$$

Next, one or more resistivity parameters are determined, including m, X, and a cation exchange capacity per unit total pore volume $Q_v$. Preferably, m, X, and $Q_v$ are all determined.

It is useful to provide a value for n and to determine a value for $C_{xo}$. A commonly used value for n is 2. Determining $C_{xo}$ may involve measuring $C_{xo}$ with a shallow-resistivity tool. After n is provided and $C_{xo}$ is determined, any saturation model can be used to determine formation factor F in step 220.

One model that can be used in accordance with this invention is the Waxman-Smits model M. H. Waxman and L. J. M. Smits, "Electrical Conductivities in Oil-Bearing Shaly Sands," *Society of Petroleum Engineers* 42nd Annual Fall Meeting held in Houston, Tex., Oct. 1–4), 1967. According to the Waxman-Smits model, $X=Q_vB$, where:

$$B = 0.15814T_C\left[1 - 0.83\exp\left(-\frac{23.25C_w}{(T_c + 21.5)}\right)\right], \quad (17)$$

where $C_w$ is the conductivity of water and $T_C$ is the temperature of the formation in degrees Celsius. In the flushed zone, water is the mud filtrate and in the virgin zone, water is the formation water. Then, X is computed accordingly. Furthermore, according to this model, $$m_{ws} = \frac{\log F_{ws}}{\log \varnothing_t}, \quad (18)$$

where $F_{ws}$ is the Waxman-Smits formation factor, and $$m_{ws} = 1.8167 + 1.6094(1 - e^{-1.2528 y}), \quad (19)$$

where $$y = Q_v \frac{\varnothing_t}{1 - \varnothing_t}. \quad (20)$$

In combination, Equations (7) and (17)–(19) can be used by a person of ordinary skill in the art to determine any or all of the desired resistivity parameters (e.g., $Q_v$ and $m_{ws}$).

Another model that may be used in accordance with this invention is the Dual Water model. (See, Clavier et al.) According to the Dual Water model: $X=(C_{wb}-C_{mf}) S_{wb}$, where $C_{mf}$ is the conductivity of mud-filtrate, $$C_{wb} = \frac{(0.00672 T_c + 0.5713) Q_V}{S_{wb}}, \quad (21)$$

where $C_{wb}$ is the clay bound water conductivity, $S_{wb}$ is the clay bound water saturation determined substantially according to: $S_{wb}=\alpha \cdot V_q \cdot Q_V$, where $\alpha$ may be determined substantially according to:

$$\alpha = \sqrt{\frac{0.245}{\gamma \bar{n}}}, \quad (22)$$

and where $\gamma$ is the activity coefficient determined substantially according to:

$$\log \gamma = \frac{a_1}{\sqrt{\bar{m}}} + a_2 \sqrt{\bar{m}} + a_3 \bar{m} + a_4 \bar{m}^2 + a_5. \quad (23)$$

Coefficients $a_1$, $a_2$, $a_3$, $a_4$, and $a_5$ are determined substantially according to:

$$a_i = b_i T_c^3 + c_i T_c^2 + d_i T_c + e_i, \quad (24)$$

where i=1, 2, 3, 4, and 5, respectively, $\bar{m}$ is a salinity of solvent, preferably in moles/kg, and the coefficients $b_i$, $c_i$, $d_i$, and $e_i$ are about:

| i | $b_i$ | $c_i$ | $d_i$ | $e_i$ |
|---|---|---|---|---|
| 1 | −6.1237e-11 | +3.6490e-08 | −1.2225e-06 | +9.7432e-04, |
| 2 | −3.1529e-08 | +8.7540e-06 | −1.3528e-03 | −2.4460e-01, |
| 3 | +1.5951e-08 | −7.0447e-06 | +1.0840e-03 | +1.0514e-01, |
| 4 | −1.0729e-09 | +5.5435e-07 | −1.0211e-04 | +4.7400e-04, and |
| 5 | +4.1937e-09 | −2.1167e-06 | +1.1317e-04 | −3-6126e-02. |

$\bar{m}$ may be determined substantially according to:

$$\bar{m} = \frac{\bar{n}}{58.443(1000 - \bar{n} 10^{-3})}. \quad (25)$$

Also, $\bar{n}$ is the salinity, preferably in moles/l, which may be determined substantially according to:

$$\bar{n} = \frac{(ppk)\rho_f}{58.433}, \quad (26)$$

where ppk is the salinity in parts per thousand and $\rho_f$ is a fluid density of the liquid phase, which includes a mixture of mud filtrate and formation water, preferably in g/cc. Vq may be determined substantially according to:

$$V_q = (4.97 \times 10^{-6} \, T_c^2) - (1.94 \times 10^{-3} \, T_c) + 0.342. \quad (27)$$

where $T_c$ is the temperature in degrees Celsius. Also, $$m_{dw} = \frac{\log F_{dw}}{\log \varnothing_t}, \quad (28)$$

where $F_{dw}$ is the Dual Water formation factor, $$m_{dw} = 1.7762 + 0.3364(1 - e^{-5.5035 y}) \quad (29)$$

and y is previously defined by Equation (20). In combination, Equations (20)–(29) can be used by a person of ordinary skill in the art to determine any or all of the resistivity parameters.

In step 230, a gas-corrected virgin zone parameter can be determined. The method preferably includes measuring a deep conductivity $C_{deep}$ (or equivalently $R_{deep}$, to calculate $C_{true}$) in the virgin zone, and determining a virgin zone water saturation $S_{wt}$ substantially according to:

$$C_{true} = S_{wt}^n \varnothing_t^m \left( C_w + \frac{X}{S_{wt}} \right), \quad (30)$$

where $C_w$ is the conductivity of water in the virgin zone. $C_{true}$ is preferably determined using a deep-resistivity measuring tool. $C_w$ (or $R_w$) may be determined in step 217 using data obtained by electrical tool measurements in step 209 in combination with values computed for $Q_v$ and $S_{xot}$ in step 215. Inputs required for that determination include $R_m$, Cali, and Di, as provided in step 212. After $S_{wt}$ is determined in step 230, one can estimate reserves and producibility of the formation, such as by calculating hydrocarbon saturation $S_{hy}$ in the virgin zone substantially according to: $S_{hy}=1-S_{wt}$.

Computation of $\phi_{bound}$ (also referred to as $V_{bound}$) in step 210 can involve, in a first step, receiving NMR data characterizing a flushed zone. The NMR data at least includes a $T_2$ distribution $P(T_2)$. In a second step, a clay bound water volume $V_{bound}$ is determined substantially according to:

$$V_{bound} = \int_{T_2 \min}^{T_2 \max} P(T_2) d T_2. \quad (31)$$

$T_2$ min is a minimum $T_2$ for clay bound water and $T_2$ max is a maximum $T_2$ for clay bound water. In a third step, a cation exchange capacity per unit total pore volume $Q_v$ is determined using a clay bound water saturation $S_{wb}$ model. $Q_v$ can be calculated using a Hill-Shirley-Klein model substantially according to:

$$Q_v = \frac{V_{bound}}{\varnothing_t (0.084 \bar{n}^{-0.5} + 0.22)}, \quad (32)$$

where $\phi_t$ is the total porosity of the formation, and $\bar{n}$ is the salinity (e.g., in meq/cc). $\phi_t$ is preferably determined from the combination NMR-density technique.

The integration limits of Equation (31) may be estimated with known values. For example, $T_2$min may be fixed at about 0.1 msecs and $T_2$ max may be fixed at about 3.0 msecs. However, as more knowledge about NMR clay bound water is gained, better estimates of $T_2$ min and $T_2$ max may be used to calculate $V_{bound}$ in accordance with this invention. Once $V_{bound}$ is determined, $S_{wb}$ may be determined substantially according to: $S_{wb}=V_{bound}/\phi_t$, where $\phi_t$ is a total porosity of the formation. Although $\phi_t$ may be an NMR-derived total porosity $\phi_{nmr}$, $\phi_t$ may also be derived from any other logging tool measurement and is best derived from the combination NMR-density technique.

Figure 3:
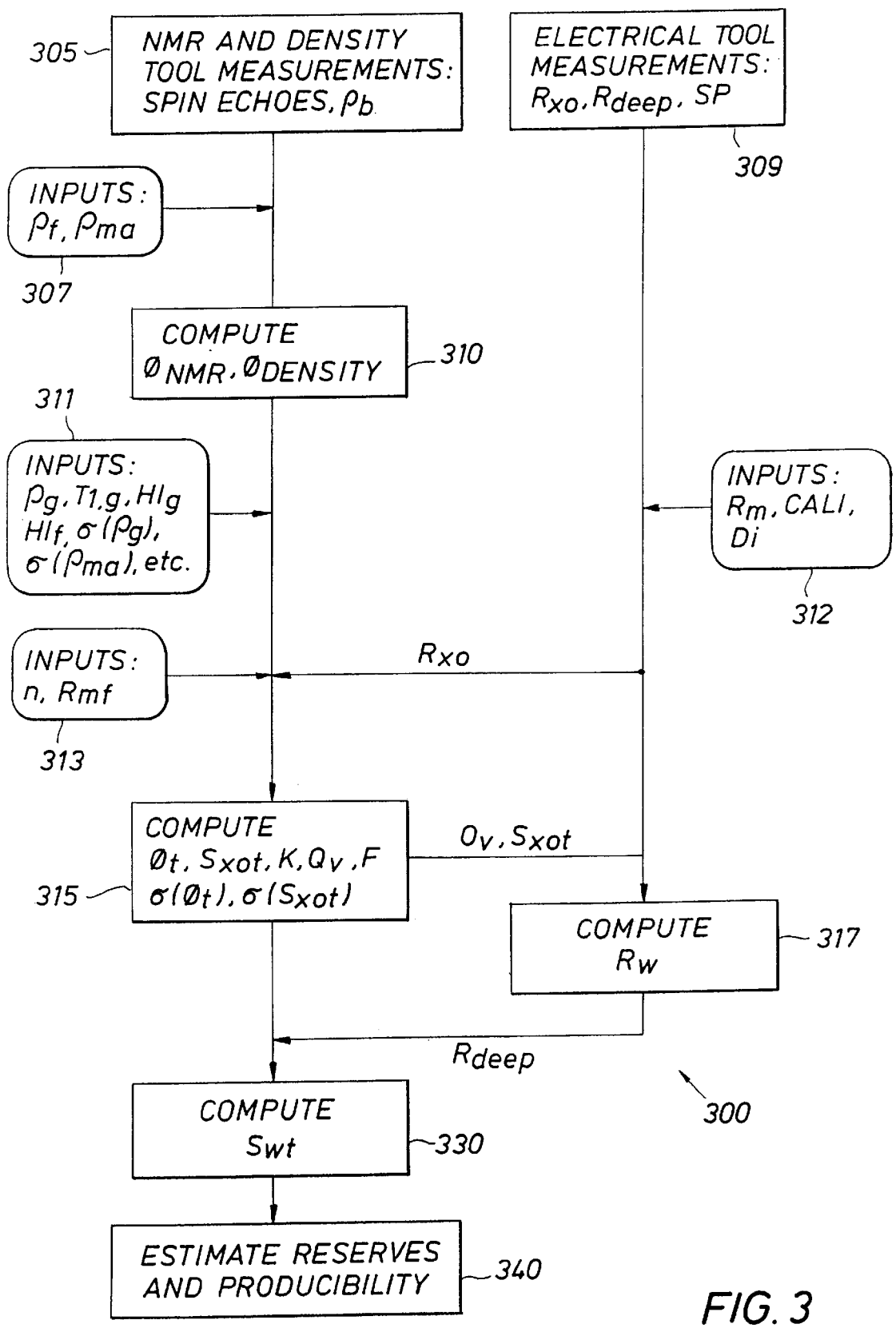
FIG. 3 is a flow chart of steps for carrying out a second illustrative embodiment of the method for characterizing a gas-bearing formation traversed by a borehole.

Another method 300 for characterizing a formation according to this invention, as shown in FIG. 3, includes the following steps. In step 310, computing at least $\phi_{nmr}$ and $\phi_{density}$ of a flushed zone; in step 309, making electrical tool measurements; in step 315, computing at least $\phi_t$, $S_{xot}$, $Q_v$, and F in the flushed zone; in step 317, computing $R_w$; in step 330, computing $S_{wt}$; and in step 340, estimating reserves and producibility of the formation.

Many of the steps of method 300, shown in FIG. 3, are the same as the steps of method 200, shown in FIG. 2. For example, before $\phi_{nmr}$ and $\phi_{density}$ are computed in steps 210 or 310, NMR data and density data that characterize the formation are preferably obtained by measurement with an NMR tool and a Density tool, as shown in steps 205 and 305. Also, the inputs used in steps 210, 215, 217 and 230 are substantially the same as the inputs used in steps 310, 315, and 317. As described above, the primary difference between method 200 and method 300 is that method 200 computes $Q_v$ from NMR data and method 300 computes $Q_v$ from shallow resistivity data $R_{xo}$.

Figure 4:
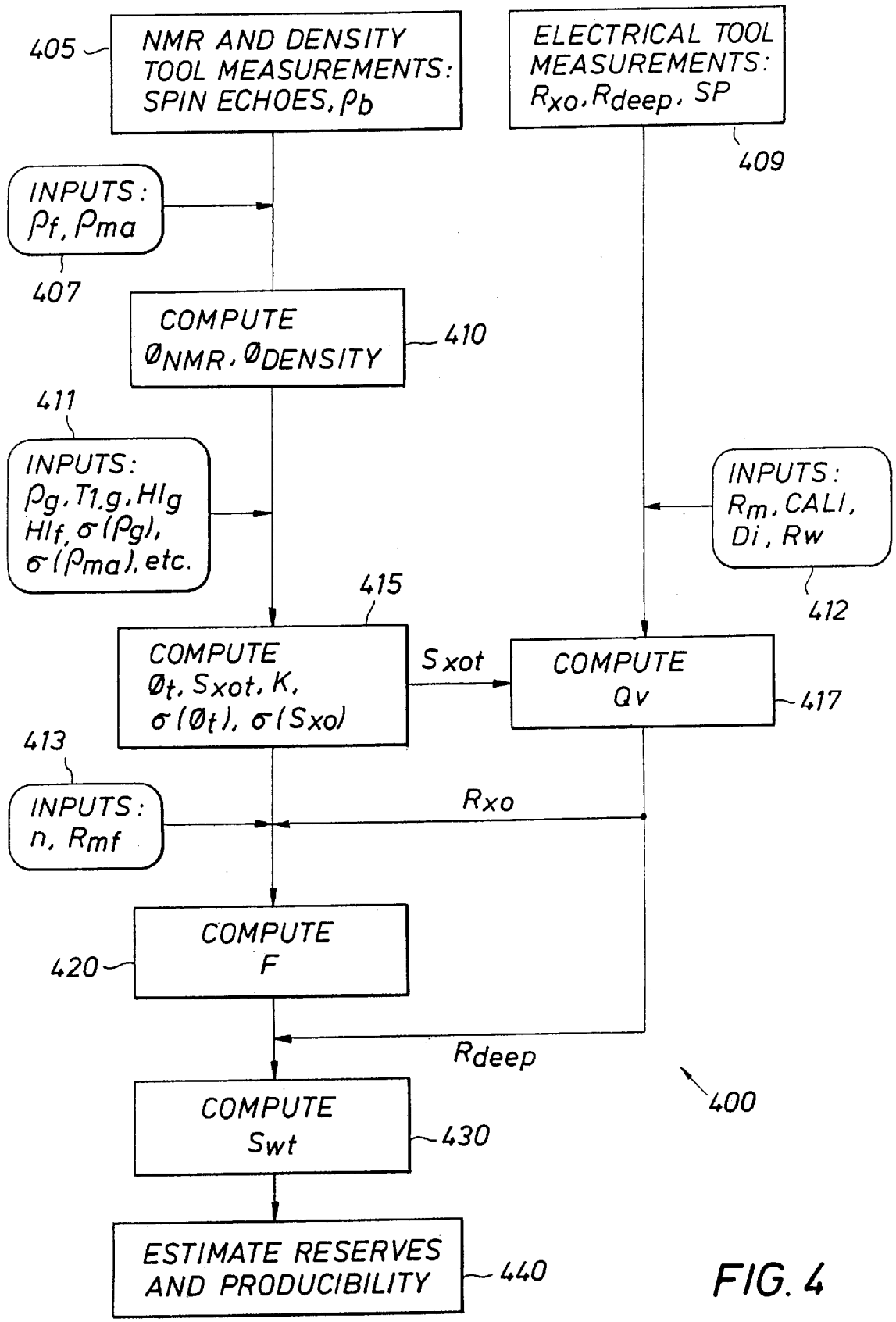
FIG. 4 is a flow chart of steps for carrying out a third illustrative embodiment of the method for characterizing a gas-bearing formation traversed by a borehole.

The third method for characterizing a formation according to this invention, as shown in FIG. 4, involves computing $Q_v$ from spontaneous potential measurement SP. Method 400 includes, in step 410, computing at least $\phi_{nmr}$ and $\phi_{density}$ of a flushed zone; in step 415, computing at least $\phi_t$ and $S_{xot}$ in the flushed zone; in step 409, making electrical tool measurements; in step 417, computing $Q_v$; in step 420, computing F; in step 430, computing $S_{wt}$; and in step 340, estimating reserves and producibility of the formation.

The method involves solving $\nabla \sigma_c \cdot \nabla V = 0$, where $\sigma_c$ is the conductivity and V is a potential everywhere in the formation. In order to solve the equation, at least two boundary conditions are used. The first boundary condition is $V_2 - V_1 =$ SSP and the second boundary condition is $J_2 - J_1 = 0$. SSP is a strength of an electro-chemical potential at the interface between the flushed zone and the virgin zone, J is the electric current density at the interface, and the subscripts 1 and 2 denote the flushed and virgin zones at the interface, respectively. SSP may be calculated with any conventional method such as with a finite element method (See, e.g., M. Y. Chen, C. Cao Minh, "Determination of Continuously Varying $R_w$ from SP," *International Symposium on Well Logging Techniques for Oilfield Development Under Waterflooding*, SPWLA, Beijing, China, September 1996), or a deconvolution method (See, e.g., J. R. Tabanou, G. Glowinsky, and G. F. Rouault, "SP Deconvolution and Quantitative Interpretation in Shaly Sands," *SPWLA 28th Symposium*, paper SS (1987)) or from published correction charts (See, e.g., F. F. Segesman,, "New SP Correction Charts," *Geophysics*, vol. 27, no. 6 (December 1962)).

SSP may be calculated by measuring the spontaneous potential SP formed between two points in the borehole, resistivity of the flushed zone $R_{xo}$, mud resistivity in the borehole $R_m$, and the borehole cross-sectional area (i.e., $$\pi \cdot \frac{Cali^2}{4}),$$

as well as resistivity in the virgin zone, resistivity of the surrounding beds, and the position of the electrochemical potential.

Alternatively, SSP may be determined substantially according to:

$$SSP = -\frac{kT}{e} \int_{C_{mf}}^{C_w} \frac{C_+ - C_-}{C} d\ln(\overline{m}\gamma), \tag{33}$$

where k is the Boltzmann constant, T is the absolute temperature of the formation, e is the electron charge, $\overline{m}$ is the salinity (moles/kg), $\gamma$ is the activity coefficient (see, e.g., Equations (23)–(26)), $C_+$ is the cation conductivity and $C_-$ is the anion conductivity, and C is the rock conductivity determined substantially according to: $C = C_+ + C_-$.

The cation conductivity $C_+$ may be determined substantially according to:

$$C_+ = S_{xot}^n \phi_t^m \left( tC_f + \frac{X}{S_{xot}} \right). \tag{34}$$

Also, the anion conductivity $C_-$ may be determined substantially according to:

$$C_- = S_{xot}^n \phi_t^m (1-t) C_f \tag{35}$$

t is the cation transference number and $C_f$ is the conductivity of the fluid at the interface. For NaCl solutions, t may be determined substantially according to:

$$t = 0.374 - 0.125 \log(\overline{m}) - 1.77e{-}3 \log^2(\overline{m}) + 4.047e{-}4(T_c^0 - 25) - 8.22e{-}7(T_c^0 - 25)^2, \tag{36}$$

and $C_f$ may be determined substantially according to:

$$\frac{1}{C_f} = 0.123 + 10^{3.562 - 0.955 \log(\overline{m})}. \tag{37}$$

$\gamma$ may be determined substantially according to Equations (23)–(25). Therefore, Equation (33) can be used to determine $C_w$ knowing $Q_v$ and $S_{xot}$ from the aforementioned techniques, or to determine $Q_v$ knowing $C_w$ and $S_{xot}$ from the aforementioned techniques.

Like method 300, many of the steps in method 400, shown in FIG. 4, are substantially the same as the steps in method 200, shown in FIG. 2. For example, the inputs provided in steps 207, 211, 212, and 213, and used in steps 210, 215, 217 and 230, are substantially the same as the inputs used in steps 410, 415, and 317. As described above, the primary difference between method 400 and the previous methods 200 and 300 is that method 400 computes $Q_v$ from spontaneous potential data SP. $R_w$ is not computed (as in steps 217 and 317 of methods 200 and 300, respectively. Rather, $R_w$ is provided in step 412 and used to compute $Q_v$ in step 417.

A method for computing bound fluid volume BFV of a formation with complex lithology is now described. The method includes receiving NMR data characterizing the flushed zone of the formation; and determining the bound fluid volume BFV of the formation. BFV is determined by summing the $BFV_i$ constituents weighted by their respective constituent volumes $V_i$, where i is the index denoting different constituents. The NMR data at least includes $P(T_2)$, which is the $T_2$ distribution.

More particularly, determining the BFV may be substantially according to:

$$BFV = \frac{\sum_i V_i \int_{T_2\min}^{T_2\text{cutoff } i} P(T_2) dT_2}{\sum_i V_i}, \qquad (38)$$

where $T_2$min is the minimum $T_2$, and $T_2$cutoffi is the cutoff $T_2$ of constituent i. Although the most accurate determination would include every constituent present in the formation, a simplified determination would only include the principal, or most abundant, constituents.

For example, if a formation is mainly formed from limestone and sandstone, the formation is said to have two principal constituents. Therefore, according to one aspect of this invention, the BFV determination using Equation (38) could be simplified to only include two terms—one for limestone and one for sandstone. That is, the BFV for a formation having two principal constituents can be expressed as:

$$BFV = \frac{V_1}{V_1 + V_2}\int_{T_2\min}^{T_2\text{cutoff }1} P(T_2) dT_2 + \frac{V_2}{V_1 + V_2}\int_{T_2\min}^{T_2\text{cutoff }2} P(T_2) dT_2, \qquad (39)$$

where $V_1$ is the volume of the first principal constituent and $V_2$ is the volume of the second principal constituent, $T_2$cutoff1 is the cutoff $T_2$ of constituent 1, $T_2$cutoff2 is the cutoff $T_2$ of constituent 2, and as above, $P(T_2)$ is the $T_2$ distribution.

The method may further include determining a permeability k of the formation according to a permeability model and the BFV calculated according to this invention. That determination may use any known permeability model.

This method may further include determining a $T_2$cutoff for the mixture substantially according to:

$$\int_{T_2\min}^{T_2\text{cutoff}} P(T_2) dT_2 = BFV, \qquad (40)$$

where $T_2$min is the known minimum $T_2$, BFV is the known bound fluid volume for the formation determined from Eq. 39, and $P(T_2)$ is the $T_2$ distribution. $T_2$min may be estimated to be about 0.3 msecs. Of course, this estimate is used only as an example and will depend on the particular formation being studied and the accuracy of the calculation desired.

TABLE 1 summarizes the different determinable parameters using different tool combinations:

TABLE 1

| Tool Combination | NMR | NMR + LDT | NMR + LDT + $R_{xo}$ | NMR + LDT + $R_{xo}$ + $R_{deep}$ + SP |
|---|---|---|---|---|
| Determinable Parameters | $\emptyset_{nmr}$ and BFV | $\emptyset_{nmr}$ BFV, k, $\emptyset_t$, $\emptyset_e$, $\emptyset_{g,xo}$ and $Q_v$ | $\emptyset_{nmr}$ BFV, k, $\emptyset_t$, $\emptyset_e$, $\emptyset_{g,xo}$, $Q_v$ and m | $\emptyset_{nmr}$ BFV, k, $\emptyset_t$, $\emptyset_e$, $\emptyset_{g,xo}$, $Q_v$, m, $R_w$ and $\emptyset_g$ |

The table includes five types of tools that can be used in accordance with the principals of this invention. However, it should be clear to a person of ordinary skill in the art that other tools could be substituted for, or used in addition to, these tools as desired. NMR is the nuclear magnetic resonance tool; LDT is the logging density tool; $R_{xo}$ is the shallow-resistivity tool for measuring flushed zone resistivity; $R_{deep}$ is the resistivity tool for measuring virgin zone resistivity. The determinable parameters, in addition to the ones described above and any computational equivalents, include $\phi_e$, which is an effective porosity.

The parameters determined according to Equations (8), (15), and (16) depend on the NMR properties and bulk densities of the fluids in the formation, the formation matrix density, the measured formation bulk densities, and the total NMR porosities. The NMR properties of the fluids and the fluid densities depend on fluid type, reservoir temperature, and pressure. For bulk fluids these properties can be estimated from published charts and literature data. See, e.g., R. Akkurt, H. J. Vinegar, P. N. Tutunjian, A. J. Guillory, "NMR Logging of Natural Gas Reservoirs," Paper N. *Transactions of the Society of Professional Well Log Analysts 36th Annual Logging Symposium* (1995); and R. L. Kleinberg and H. J. Vinegar, "NMR Properties of Reservoir Fluids," *The Log Analyst*, (November–December, 1996). Furthermore, a recent paper shows that the methane gas longitudinal relaxation times in rocks are reduced from their bulk values by surface relaxation. See, C. Straley, "An Experimental Investigation of Methane in Rock Materials," Paper AA, *Transactions of the Society of Professional Well Log Analysts 38th Annual Logging Symposium* (1997). This effect adds additional uncertainty to our estimation of in-situ NMR relaxation times of reservoir gas.

The inputs used by Equations (8), (15), and (16) are $\rho_b$, $\rho_{ma}$, $\rho_f$, $\rho_g$, $T_{l,gas}$, $(HI)_g$, $(HI)_f$, $\phi_{nmr}$, and WT. The uncertainties in the outputs (e.g., see steps 215, 315, and 415) can be computed from the uncertainties assigned to each of the inputs, which depend on the logging environment (e.g., see steps 211, 311, and 411). For example, in a shaly sand development well a log analyst or geologist might reasonably assign a value to the formation matrix density that assumes a small uncertainty (e.g., $\rho_{ma}$=2.65±0.03 g/cm³). In a shaly sand exploration well with unknown mineralogy the formation matrix density might reasonably be assigned a greater uncertainty (e.g., $\rho_{ma}$=2.65±0.05 g/cm³). The input uncertainties usually reflect our lack of detailed knowledge of a particular parameter. There are also uncertainties in measured log responses. These are due to measurement errors and to statistical errors arising from random noise. For example, a formation bulk density tool measurement may have a total measurement uncertainty of ±0.01 g/cm³.

In light of these uncertainty factors, it would be desirable to estimate the magnitude of the uncertainties of the resistivity parameters determined from Equations (8), (15), and (16).

Thus, in accordance with the principles of this invention, a method for analyzing the uncertainty of resistivity parameters is provided. The method includes calculating the variance of a resistivity parameter substantially according to:

$$\sigma^2(f) \cong \sum_{i=1}^{n} \left(\frac{\partial f}{\partial x_i}\right)^2_{x_i^*} \sigma^2(x_i), \qquad (41)$$

where $f$ is a parameter that is a function of n variables $x_n$, $\sigma^2(f)$ is a variance of $f$, and $x_i^*$ is a best estimate for each of the n variables. The best estimates are preferably the statistical expectation values of the variables. However, in practice these values are user-assigned inputs. Equation (41) assumes that the uncertainties of all input parameters are statistically independent and that third and higher order terms in the deviations $(x_1-x_i)^*$ can be neglected. The variance $\sigma^2(x_i)$ in each input is the square of the uncertainty assigned to that input and the variance $\sigma^2(f)$ is the square of the uncertainty in $f$. See, R. Freedman and B. E. Ausburn, "The Waxman-Smits Equation for Shaly Sands: I. Simple Methods of Solution: II. Error Analysis: *The Log Analyst*, at 11–23 (March–April, 1985).

$f$ may be any calculable parameter, and $f$ is preferably a gas-corrected total porosity $\phi_t$, a gas volume of the flushed zone $V_{g,xo}$, or a flushed zone gas saturation $S_{g,xo}$. For calculation of these outputs, useful quantities $N_1$, $N_2$, $a^0$, and $D$ are defined substantially according to:

$$N_1 \equiv \phi_{density} - \frac{\phi_{nmr}}{(HI)_f}, \tag{42}$$

$$N_2 \equiv 1 - \frac{(HI)_g P_g}{(HI)_f}, \tag{43}$$

$$a^0 \equiv \frac{(HI)_g}{(HI)_f}, \text{ and} \tag{44}$$

$$D \equiv 1 - \frac{(HI)_g P_g}{(HI)_f} + \lambda, \tag{45}$$

where $(HI)_g$, $(HI)_f$, $P_g$, $\lambda$, $\phi_{density}$, and $\phi_{nmr}$ are defined as above.

When calculating the variance of $\phi_t$ according to Equation (41), the following partial differential equation may be used:

$$\frac{\partial \phi_t}{\partial \rho_b} = \frac{N_2}{D(\rho_f - \rho_{ma})}, \tag{46}$$

$$\frac{\partial \phi_t}{\partial \rho_f} = \frac{N_1 N_2 (\rho_g - \rho_{ma})}{D^2(\rho_f - \rho_{ma})^2} + \frac{N_2(\rho_{ma} - \rho_b)}{D(\rho_f - \rho_{ma})^2}, \tag{47}$$

$$\frac{\partial \phi_t}{\partial \rho_g} = \frac{N_1 N_2}{D^2(\rho_{ma} - \rho_f)}, \tag{48}$$

$$\frac{\partial \phi_t}{\partial \rho_{ma}} = \frac{N_1 N_2 (\rho_f - \rho_g)}{D^2(\rho_f - \rho_{ma})^2} + \frac{N_2(\rho_b - \rho_f)}{D(\rho_f - \rho_{ma})^2}, \tag{49}$$

$$\frac{\partial \phi_t}{\partial T_{l,g}} = \frac{W a^0 \lambda N_1 e^{-\frac{WT}{T_{l,g}}}}{T_{l,g}^2 D^2}, \tag{50}$$

$$\frac{\partial \phi_t}{\partial (HI)_f} = \frac{-\lambda \phi_{nmr}}{D(HI)_f^2} + \frac{\lambda P_g N_1 a^0}{D^2(HI)_f}, \tag{51}$$

$$\frac{\partial \phi_t}{\partial (HI)_g} = \frac{-P_g \lambda N_1}{D^2(HI)_f}, \text{ and} \tag{52}$$

$$\frac{\partial \phi_t}{\partial \phi_{nmr}} = \frac{\lambda}{D(HI)_f}. \tag{53}$$

When calculating the variance of $V_{g,xo}$ according to Equation (41), the following partial differential equations may be used:

$$\frac{\partial V_{g,xo}}{\partial \rho_b} = \frac{1}{D(\rho_f - \rho_{ma})}, \tag{54}$$

$$\frac{\partial V_{g,xo}}{\partial \rho_f} = \frac{N_1(\rho_g - \rho_{ma})}{D^2(\rho_f - \rho_{ma})^2} + \frac{(\rho_{ma} - \rho_b)}{D(\rho_f - \rho_{ma})^2}, \tag{55}$$

$$\frac{\partial V_{g,xo}}{\partial \rho_g} = \frac{N_1}{D^2(\rho_{ma} - \rho_f)}, \tag{56}$$

$$\frac{\partial V_{g,xo}}{\partial \rho_{ma}} = \frac{N_1(\rho_f - \rho_g)}{D^2(\rho_f - \rho_{ma})^2} + \frac{(\rho_b - \rho_f)}{D(\rho_f - \rho_{ma})}, \tag{57}$$

$$\frac{\partial V_{g,xo}}{\partial T_{l,gas}} = -\frac{W a^0 N_1 e^{-\frac{WT}{T_{l,gas}}}}{T_{l,gas}^2 D^2}, \tag{58}$$

$$\frac{\partial V_{g,xo}}{\partial (HI)_f} = \frac{\phi_{nmr}}{D(HI)_f^2} - \frac{a^0 P_g N_1}{D^2(HI)_f}, \tag{59}$$

$$\frac{\partial V_{g,xo}}{\partial (HI)_g} = \frac{P_g N_1}{D^2(HI)_f}, \text{ and} \tag{60}$$

$$\frac{\partial V_{g,xo}}{\partial \phi_{nmr}} = -\frac{1}{D(HI)_f}. \tag{61}$$

The variance of $S_{g,xo}$ may also be directly calculated substantially according to Equation (41) or indirectly calculated substantially according to:

$$\sigma^2(S_{g,xo}) = \frac{V_{g,xo} \sigma^2(\hat{u}_t)}{\phi_t^4} + \frac{\sigma^2(V_{g,xo})}{\phi_t^2}, \tag{62}$$

where $\sigma^2(\phi_t)$ and $\sigma^2(V_{g,xo})$ are calculated substantially according to Equations (41) in conjunction with (42)–(53) and (54)–(61), respectively.

The following examples use synthetic data to show that these calculated outputs are relatively insensitive to realistic input uncertainties.

HIGH POROSITY SHALY GAS SAND EXAMPLES

TABLE 2 contains synthetic data inputs used to compute the outputs shown in TABLE 3 for twelve high-porosity shaly gas sand examples. The examples illustrate the magnitude of the errors in $\phi_t$ and $V_{g,xo}$ that arise from realistic uncertainties in the inputs.

Examples 1–3 in TABLES 2 and 3 assume that the matrix density $\rho_{ma}$ is known to within $\pm 0.03$ g/cm$^3$. Examples 4–6 are identical to Examples 1–3, except that the wait time of the pulse sequence was reduced to 2 seconds. Examples 7–12 include $\rho_{ma}$ and $\phi_{nmr}$ with larger uncertainties. The uncertainties $\sigma(\phi_t)$ in TABLE 2 range between 1.3 and 1.9 p.u. and the uncertainties $\sigma(V_{g,xo})$ range between 2.0 and 2.9 p.u. Calculated $\phi_{density}$, $\phi_t$, $V_{g,xo}$, and $S_{g,xo}$, and error analysis $\sigma(\phi_t)$ and $\sigma(V_{g,xo})$ are shown in TABLE 3.

Note that the uncertainties in $\phi_t$ and $V_{g,xo}$ are relatively small considering there exist uncertainties in eight of the inputs.

TABLE 2

Synthetic Inputs for High-Porosity Shaly Gas Sand

| Ex. | $\rho_b$ | $\rho_{ma}$ | $\rho_f$ | $\rho_g$ | $T_{1,gas}$ | $(HI)_g$ | $(HI)_f$ | $\phi_{nmr}$ | WT |
|---|---|---|---|---|---|---|---|---|---|
| 1 | 2.2 ± 0.01 | 2.65 ± 0.0 | 1.0 ± 0.1 | 0.2 ± 0.1 | 4.0 ± 1.0 | 0.4 ± 0.1 | 1.0 ± 0.1 | 0.10 ± 0.01 | 4.0 |
| 2 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.15 ± 0.01 | 4.0 |
| 3 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.20 ± 0.01 | 4.0 |
| 4 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.10 ± 0.01 | 2.0 |
| 5 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.15 ± 0.01 | 2.0 |
| 6 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.20 ± 0.01 | 2.0 |
| 7 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.10 ± 0.01 | 4.0 |
| 8 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.15 ± 0.01 | 4.0 |
| 9 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.20 ± 0.01 | 4.0 |
| 10 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.10 ± 0.01 | 2.0 |
| 11 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.15 ± 0.01 | 2.0 |
| 12 | 2.2 ± 0.01 | 2.65 + 0.0 | 1.0 ± 0.1 | 0.2 ± 0.1 | 4.0 ± 1.0 | 0.4 ± 0.1 | 1.0 ± 0.1 | 0.20 ± 0.01 | 2.0 |

TABLE 3

Synthetic Outputs for High-Porosity Shaly Gas Sand

| Ex. | $\phi_{density}$ | $\phi_t$ | $V_g$ | $S_{g,xo}$ | $\sigma(\phi_t)$ | $\sigma(V_{g,xo})$ |
|---|---|---|---|---|---|---|
| 1 | 0.27 | 0.205 | 0.14 | 0.69 | 0.013 | 0.020 |
| 2 | 0.27 | 0.224 | 0.10 | 0.44 | 0.013 | 0.021 |
| 3 | 0.27 | 0.244 | 0.06 | 0.24 | 0.014 | 0.023 |
| 4 | 0.27 | 0.210 | 0.13 | 0.62 | 0.013 | 0.017 |
| 5 | 0.27 | 0.228 | 0.09 | 0.41 | 0.013 | 0.019 |
| 6 | 0.27 | 0.246 | 0.06 | 0.22 | 0.015 | 0.022 |
| 7 | 0.27 | 0.205 | 0.14 | 0.68 | 0.019 | 0.027 |
| 8 | 0.27 | 0.224 | 0.10 | 0.44 | 0.018 | 0.027 |
| 9 | 0.27 | 0.244 | 0.06 | 0.24 | 0.019 | 0.029 |
| 10 | 0.27 | 0.210 | 0.13 | 0.62 | 0.018 | 0.024 |
| 11 | 0.27 | 0.228 | 0.09 | 0.41 | 0.018 | 0.025 |
| 12 | 0.27 | 0.246 | 0.06 | 0.22 | 0.019 | 0.027 |

TABLE 5

Synthetic Outputs for Low-Porosity Shaly Gas Sand

| Ex. | $\phi_{density}$ | $\phi_t$ | $V_{g,xo}$ | $S_g$ | $\sigma(\phi_t)$ | $\sigma(V_{g,xo})$ |
|---|---|---|---|---|---|---|
| 1 | 0.09 | 0.083 | 0.017 | 0.21 | 0.012 | 0.018 |
| 2 | 0.09 | 0.079 | 0.025 | 0.32 | 0.012 | 0.018 |
| 3 | 0.09 | 0.075 | 0.033 | 0.44 | 0.012 | 0.017 |
| 4 | 0.09 | 0.083 | 0.016 | 0.19 | 0.012 | 0.017 |
| 5 | 0.09 | 0.080 | 0.023 | 0.29 | 0.012 | 0.016 |
| 6 | 0.09 | 0.076 | 0.031 | 0.41 | 0.012 | 0.016 |
| 7 | 0.09 | 0.083 | 0.017 | 0.21 | 0.019 | 0.027 |
| 8 | 0.09 | 0.079 | 0.025 | 0.32 | 0.019 | 0.027 |
| 9 | 0.09 | 0.075 | 0.033 | 0.44 | 0.019 | 0.027 |
| 10 | 0.09 | 0.083 | 0.016 | 0.19 | 0.019 | 0.025 |
| 11 | 0.09 | 0.080 | 0.023 | 0.29 | 0.019 | 0.025 |
| 12 | 0.09 | 0.076 | 0.031 | 0.41 | 0.019 | 0.025 |

LOW-POROSITY SHALY GAS SAND EXAMPLES

TABLES 4 and 5 are analogous to TABLES 2 and 3, except that the twelve examples are for a low-porosity shaly gas sand formation. These examples also assume realistic uncertainties in the input variables.

Again, the uncertainties in $\phi_t$ and $V_{g,xo}$ are relatively small considering there exist uncertainties in eight of the inputs. However, gas volume uncertainties $\sigma(V_{g,xo})$ listed in TABLE 5 are of the same order of magnitude as gas volume uncertainties $V_{g,xo}$, which means that gas volume quantification is more difficult in low-porosity zones.

It will be understood that the foregoing is only illustrative of the principles of the invention, and that various modifications can be made by those skilled in the art without departing from the scope and spirit of the invention. For example, Equations (8), (15), and (16) assume that wait time WT is sufficiently long to appreciably polarize the liquid phase. If this is not the case, these equations can be modified by replacing every occurrence of $(HI)_f$ by the product $(HI)_f \cdot P_f$, where $P_f$ is a polarization function. Furthermore, if the well is drilled with oil-based mud and the reservoir is at an irreducible water saturation, then $\phi_{nmr}$ can be corrected for insufficient wait time by applying an oil-base mud filtrate polarization correction factor to the free-fluid porosity. The corrected $\phi_{nmr}$ can be then be used analogously in Equations

TABLE 4

Synthetic Data Inputs for Low-Porosity Shaly Gas Sand

| Ex. | $\rho_b$ | $\rho_{ma}$ | $\rho_f$ | $\rho_g$ | $T_{1,gas}$ | $(HI)_g$ | $(HI)_f$ | $\phi_{mar}$ | WT |
|---|---|---|---|---|---|---|---|---|---|
| 1 | 2.5 ± 0.01 | 2.65 ± 0.0 | 1.0 ± 0.1 | 0.2 ± 0.1 | 4.0 ± 1.0 | 0.4 ± 0.1 | 1.0 ± 0.1 | 0.07 ± 0.01 | 4.0 |
| 2 | 2.5 ± 0.01 | 2.65 + 0.0 | 1.0 ± 0.1 | 0.2 ± 0.1 | 4.0 + 1.0 | 0.4 ± 0.1 | 1.0 ± 0.1 | 0.06 ± 0.01 | 4.0 |
| 3 | 2.5 ± 0.0l | 2.65 + 0.0 | 1.0 ± 0.1 | 0.2 ± 0.1 | 4.0 + 1.0 | 0.4 ± 0.1 | 1.0 ± 0.1 | 0.05 ± 0.01 | 4.0 |
| 4 | 2.5 ± 0.01 | 2.65 + 0.0 | 1.0 ± 0.1 | 0.2 ± 0.1 | 4.0 + 1.0 | 0.4 ± 0.1 | 1.0 ± 0.1 | 0.07 ± 0.01 | 2.0 |
| 5 | 2.5 ± 0.01 | 2.65 + 0.0 | 1.0 ± 0.1 | 0.2 ± 0.1 | 4.0 + 1.0 | 0.4 ± 0.1 | 1.0 ± 0.1 | 0.06 ± 0.01 | 2.0 |
| 6 | 2.5 ± 0.0l | 2.65 + 0.0 | 1.0 ± 0.1 | 0.2 ± 0.1 | 4.0 + 1.0 | 0.4 ± 0.1 | 1.0 ± 0.1 | 0.05 ± 0.01 | 2.0 |
| 7 | 2.5 ± 0.01 | 2.65 + 0.0 | 1.0 ± 0.1 | 0.2 ± 0.1 | 4.0 + 1.0 | 0.4 ± 0.1 | 1.0 ± 0.1 | 0.07 ± 0.015 | 4.0 |
| 8 | 2.5 ± 0.01 | 2.65 + 0.0 | 1.0 ± 0.1 | 0.2 ± 0.1 | 4.0 + 1.0 | 0.4 ± 0.1 | 1.0 ± 0.1 | 0.06 ± 0.015 | 4.0 |
| 9 | 2.5 ± 0.01 | 2.65 + 0.0 | 1.0 ± 0.1 | 0.2 ± 0.1 | 4.0 + 1.0 | 0.4 ± 0.1 | 1.0 ± 0.1 | 0.05 ± 0.015 | 4.0 |
| 10 | 2.5 ± 0.0l | 2.65 + 0.0 | 1.0 ± 0.1 | 0.2 ± 0.1 | 4.0 + 1.0 | 0.4 ± 0.1 | 1.0 ± 0.1 | 0.07 ± 0.015 | 2.0 |
| 11 | 2.5 ± 0.01 | 2.65 + 0.0 | 1.0 ± 0.1 | 0.2 ± 0.1 | 4.0 + 1.0 | 0.4 ± 0.1 | 1.0 ± 0.1 | 0.06 ± 0.015 | 2.0 |
| 12 | 2.5 ± 0.01 | 2.65 + 0.0 | 1.0 ± 0.1 | 0.2 ± 0.1 | 4.0 + 1.0 | 0.4 ± 0.1 | 1.0 ± 0.1 | 0.05 ± 0.015 | 2.0 |

(8), (15), and (16). Although corrections for insufficient polarization of the mud filtrate can be applied, a job planner is preferably used before logging to help select a wait time that ensures sufficient polarization of the filtrate.

Furthermore, determining, calculating, solving, or using any of the equations or mathematical relationships included herein may be performed with a commercially available processor downhole or uphole, as desired.

We claim:

1. A method for characterizing a gas-bearing formation traversed by a borehole comprising:

computing an NMR-derived total porosity $\phi_{nmr}$ and a density-derived total porosity $\phi_{density}$ of said flushed zone;

determining a gas-corrected total porosity $\phi_t$ using said $\phi_{nmr}$ and said $\phi_{density}$;

determining a gas-corrected total water saturation $S_{xot}$ of said flushed zone using said $\phi_{nmr}$ and said $\phi_{density}$; and determining a resistivity parameter using:

$$C_{ox} = S_{xot}^n \phi_t^m \left( C_{mf} + \frac{X}{S_{xot}} \right),$$

where n is a saturation exponent, m is a model-dependent cementation exponent, $C_{xo}$ is a conductivity of said flushed zone, $C_{xo}$ being equal to $1/R_{xo}$, where $R_{xo}$ is a flushed zone resistivity, $C_{mf}$ is a mud filtrate conductivity, $C_{mf}$ being equal to $1/R_{mf}$, where $R_{mf}$ is a resistivity of said mud filtrate, and where X is a model-dependent clay conductivity.

2. The method of claim 1 further comprising measuring a first portion of said earth formation with a nuclear magnetic resonance tool to obtain NMR data.

3. The method of claim 2 further comprising measuring a second portion of said earth formation with a density tool to obtain density data.

4. The method of claim 3 wherein said first portion and said second portion are substantially the same.

5. The method of claim 1 wherein said determining said $\phi_t$ comprises:

$$\phi_t = \frac{\phi_{density}\left(1 - \frac{(HI)_g P_g}{(HI)_f}\right) + \phi_{nmr}\left(\frac{\lambda}{(HI)_f}\right)}{\left(1 - \frac{(HI)_g P_g}{(HI)_f}\right) + \lambda},$$

where $(HI)_g$ is a Hydrogen Index of a gas, $(HI)_f$ is a Hydrogen Index of a liquid phase comprising mud filtrate and formation water, $P_g$ is a gas polarization function, which is defined as $1-\exp(-WT/T_{l,gas})$, where WT is a wait time for a pulse sequence and $T_{l,gas}$ is a gas longitudinal relaxation time at said condition, $$\lambda = \frac{\rho_f - \rho_g}{\rho_{ma} - \rho_f},$$

where $\rho_f$ is a density of said liquid phase, $\rho_{ma}$ is a formation matrix density, $\rho_g$ is a density of said gas, and $$\phi_{density} = \frac{\rho_b - \rho_{ma}}{\rho_f - \rho_{ma}},$$

where $\rho_b$ is a formation bulk density.

6. The method of claim 5 for use in complex lithology wherein said method further comprises:

providing lithology-dependent data to determine a volume $V_i$ of a formation constituent i; and determining said matrix density $\rho_{ma}$ using said lithology-dependent data substantially according to:

$$\rho_{ma} = \frac{\sum_i V_i \rho_i}{\sum_i V_i},$$

where $\rho_i$ is a density of said constituent i.

7. The method of claim 1 wherein said determining said $\phi_t$ is substantially according to:

$$\phi_t = \phi_{density} * w + (1-w) * \frac{\phi_{nmr}}{(HI)_f},$$

where said w is determined substantially according to:

$$w = \frac{1 - \frac{(HI)_g * P_g}{(HI)_f}}{\left(1 - \frac{(HI)_g * P_g}{(HI)_f}\right) + \lambda},$$

where $(HI)_g$ is a Hydrogen Index of a gas, $(HI)_f$ is a Hydrogen Index of a liquid phase comprising mud filtrate and formation water, $P_g$ is a gas polarization function, which is defined as $1-\exp(-WT/T_{l,gas})$, where WT is a wait time for a pulse sequence and $T_{l,gas}$ is a gas longitudinal relaxation time, $$\lambda = \frac{\rho_f - \rho_g}{\rho_{ma} - \rho_f},$$

where $\rho_f$ is a density of said liquid phase, $\rho_{ma}$ is a formation matrix density, $\rho_g$ is a density of said gas, and $$\phi_{density} = \frac{\rho_b - \rho_{ma}}{\rho_f - \rho_{ma}},$$

where $\rho_b$ is a formation bulk density.

8. The method of claim 1 for use in complex lithology wherein said method further comprises:

providing lithology-dependent data to determine a volume $V_i$ of a formation constituent i; and determining said matrix density $\rho_{ma}$ using said lithology-dependent data substantially according to:

$$\rho_{ma} = \frac{\sum_i V_i \rho_i}{\sum_i V_i},$$

where $\rho_i$ is a density of said formation constituent i.

9. The method of claim 1 wherein said determining said $S_{xot}$ is substantially according to: $S_{xot}=V_{xot}/\phi_t$, where $V_{xot}$ is a total water volume of said flushed zone.

10. The method of claim 9 wherein said determining said $V_{xot}$ is substantially according to: $V_{xot}=\phi_t-V_{gxo}$, $V_{gxo}$ is a gas volume of said flushed zone.

11. The method of claim 10 wherein said $V_{gxo}$ is determined substantially according to:

$$V_{g,xo} \frac{\varnothing_{density} - \frac{\varnothing_{nmr}}{(HI)_f}}{\left(1 - \frac{(HI)_g P_g}{(HI)_f}\right) + \lambda}.$$

12. The method of claim 9 wherein said $V_{g,xo}$ is determined substantially according to: $V_{g,xo}=S_{g,xo}\cdot\phi_t$, where $S_{g,xo}$ is a flushed zone gas saturation determined substantially according to:

$$S_{g,xo} = \frac{\varnothing_{density} - \frac{\varnothing_{nmr}}{(HI)_f}}{\varnothing_{density} * \left(1 - \frac{(HI)_g * P_g}{(HI)_f}\right) + \frac{\lambda * \varnothing_{nmr}}{(HI)_f}}.$$

13. The method of claim 1 wherein said determining a resistivity parameter comprises calculating a parameter selected from a group consisting of said m, said X, and a cation exchange capacity per unit total pore volume $Q_v$.

14. The method of claim 13 wherein said determining a resistivity parameter comprises using a Waxman-Smits model.

15. The method of claim 14 wherein said using a Waxman-Smits model comprises using $X=Q_v B$, where $$B = 0.15814 T_C\left[\left(1 - 0.83\exp-\frac{23.25 C_{mf}}{(T_C+21.5)}\right)\right],$$

where $C_{mf}$ is a conductivity of water, $T_C$ is a temperature of said formation in degrees Celsius, and $$m_{ws} = \frac{\log F_{ws}}{\log \varnothing_t},$$

where $F_{ws}$ is a Waxman-Smits formation factor, $$m_{ws}=1.8167+1.6094\,(1-e^{-1.2528 y}),$$

and $$y = Q_v \frac{\varnothing_t}{1-\varnothing_t}.$$

16. The method of claim 13 wherein said determining a resistivity parameter comprises using a Dual Water model.

17. The method of claim 16 wherein said using a Dual Water model comprises using:

$$X=(C_{wb}-C_{mf})S_{wb},$$

where $C_{mf}$ is a conductivity of mud-filtrate, $$C_{wb} = \frac{(0.00672 T_C + 0.5713) Q_V}{S_{wb}},$$

where $C_{wb}$ is a clay bound water conductivity, $S_{wb}$ is a clay bound water saturation, $T_C$ is a temperature in degrees Celsius of said formation, and $$m_{dw} = \frac{\log F_{dw}}{\log \varnothing_t},$$

where $F_{dw}$ is a Dual Water formation factor, $$m_{dw}=1.7762+0.3364(1-e^{-5.5035 y})$$

and $$y = Q_v \frac{\varnothing_t}{1-\varnothing_t}.$$

18. The method of claim 13 wherein said determining a resistivity parameter further comprises:
 determining a true formation conductivity $C_{true}$ in said virgin zone; and
 determining a virgin zone water saturation $S_{wt}$ substantially according to:

$$C_{true} = S_{wt}^n \varnothing_t^m \left(C_w + \frac{X}{S_{wt}}\right),$$

where said $C_w$ is a conductivity of water in said virgin zone.

19. The method of claim 18 wherein said determining $C_{true}$ in said virgin zone is performed using a deep-resistivity measuring tool.

20. The method of claim 19 further comprising determining $C_w$ using an electrochemical potential model and SP logging data.

21. The method of claim 20 further comprising determining a hydrocarbon saturation $S_{hy}$ in said virgin zone substantially according to: $S_{hy}=1-S_{wt}$.

22. A method for characterizing a formation traversed by a borehole comprising:
 receiving NMR data characterizing a flushed zone, said NMR data at least comprising $P(T_2)$, which is a $T_2$ distribution;
 determining a clay bound water volume $V_{bound}$ substantially according to:

$$V_{bound} = \int_{T_2 \min}^{T_2 \max} P(T_2)\, dT_2,$$

where $T_2\min$ is a minimum $T_2$ for clay bound water and $T_2\max$ is a maximum $T_2$ for clay bound water; and
 determining a cation exchange capacity per unit total pore volume $Q_v$ using a clay bound water saturation $S_{wb}$ model.

23. The method of claim 22 further comprising determining said $S_{wb}$ substantially according to: $S_{wb}=V_{bound}/\phi_t$, where $\phi_t$ is a hydrocarbon corrected total porosity of said formation.

24. The method of claim 23 wherein said $\phi_t$ is derived from $\phi_{nmr}$ and $\phi_{density}$.

25. The method of claim 23 wherein said $\phi_t$ is substantially determined according to:

$$\varnothing_t = \frac{\varnothing_{density}\left(1 - \frac{(HI)_g P_g}{(HI)_f}\right) + \varnothing_{nmr}\left(\frac{\lambda}{(HI)_f}\right)}{\left(1 - \frac{(HI)_g P_g}{(HI)_f}\right) + \lambda},$$

where $(HI)_g$ is a Hydrogen Index of a gas, $(HI)_f$ is a Hydrogen Index of a liquid phase comprising mud filtrate and formation water, $P_g$ is a gas polarization function, which is defined as $1-\exp(-WT/T_{1,gas})$, where WT is a wait time for a pulse sequence and $T_{1,gas}$ is a gas longitudinal relaxation time at said condition, $$\lambda = \frac{\rho_f - \rho_g}{\rho_{ma} - \rho_f},$$

where $\rho_f$ is a density of said liquid phase, $\rho_{ma}$ is a formation matrix density, $\rho_g$ is a density of said gas, and $$\varnothing_{density} = \frac{\rho_b - \rho_{ma}}{\rho_f - \rho_{ma}},$$

where $\rho_b$ is a formation bulk density.

26. The method of claim 23 wherein said determining said $Q_v$ is substantially according to: $Q_v = S_{wb}/\alpha \, V_q$, where $\alpha$ is a Gouy expansion factor of a clay diffuse layer and $V_q$ is determined substantially according to: $V_q$=4.97e–06 $T_c^2$–1.94e–03 $T_c$+0.342.

27. The method of claim 26 wherein said $\alpha$ is determined substantially according to:

$$\alpha = \sqrt{\frac{0.245}{\gamma \bar{n}}},$$

where $\gamma$ is an activity coefficient and said $\bar{n}$ is a salinity.

28. The method of claim 27 wherein said $\bar{n}$ is determined substantially according to:

$$\bar{n} = \frac{ppk\rho_f}{58.433},$$

where said ppk is a salinity and $\rho_f$ is a liquid phase density.

29. The method of claim 27 wherein said $\gamma$ is determined substantially according to:

$$\log \gamma = \frac{a_1}{\sqrt{\bar{m}}} + a_2\sqrt{\bar{m}} + a_3\bar{m} + a_4\bar{m}^2 + a_5,$$

where said coefficients $a_1$, $a_2$, $a_3$, $a_4$, and $a_5$, are determined substantially according to:

$$a_i = b_i T_c^3 + c_i T_c^2 + d_i T_c + e_i,$$

where i=1, 2, 3, 4, and 5, respectively, $\bar{m}$ is a salinity of solvent determined substantially according to:

$$\bar{m} = \frac{\bar{n}}{58.443(1000 - \bar{n}10^{-3})},$$

and where said coefficients $b_i$, $c_i$, $d_i$, and $e_i$ are about:

| i | $b_i$ | $c_i$ | $d_i$ | $e_i$ |
|---|---|---|---|---|
| 1 | –6.1237e-11 | +3.6490e-08 | –1.2225e-06 | +9.7432e-04, |
| 2 | –3.1529e-08 | +8.7540e-06 | –1.3528e-03 | –2.4460e-01, |
| 3 | +1.5951e-08 | –7.0447e-06 | +1.0840e-03 | +1.0514e-01, |
| 4 | –1.0729e-09 | +5.5435e-07 | –1.0211e-04 | +4.7400e-04, and |
| 5 | +4.1937e-09 | –2.1167e-06 | +1.1317e-04 | –3-6126e-02. |

30. The method of claim 22 wherein said determining said $Q_v$ comprises using a Hill-Shirley-Klein model substantially according to:

$$Q_v = \frac{V_{bound}}{\varnothing_t(0.084\bar{n}^{-0.5} + 0.22)},$$

where $\phi_t$ is a total porosity of said formation, and $\bar{n}$ is a salinity.

31. A method for characterizing a formation traversed by a borehole comprising:

receiving SP logging data; and determining a cation exchange capacity per unit total pore volume $Q_v$ or a resistivity $R_w$ using an electrochemical potential model and said SP logging data.

32. The method of claim 31 wherein said using said SP logging data comprises solving $\nabla \sigma_c \cdot \nabla V = 0$, where $\sigma_c$ is a conductivity and V is a potential everywhere in space, said solving comprising using at least a first boundary condition and a second boundary condition, said first boundary condition being $V_2 - V_1 = SSP$ and said second boundary condition being $J_2 - J_1 = 0$, where SSP is a strength of an electrochemical potential at an interface between a flushed zone and a virgin zone, J is an electric current density at said interface, and where subscripts 1 and 2 denote said flushed and virgin zones at said interface, respectively.

33. The method of claim 32 wherein said solving comprises calculating said SSP using a method selected from a group consisting of a finite element method and a deconvolution method.

34. The method of claim 33 wherein said =calculating said SSP further comprises measuring a spontaneous potential SP formed between two points in said borehole, a resistivity of said flushed zone, a resistivity in said virgin zone, a position of said electrochemical potential, a mud resistivity in said borehole, and a borehole cross-sectional area.

35. The method of claim 34 wherein said method of determining said SSP is substantially according to:

$$SSP = -\frac{kT}{e} \int_{C_{mf}}^{C_w} \frac{C_+ - C_-}{C} d\ln(\bar{m}\gamma),$$

where k is a Boltzmann constant, T is an absolute temperature of said formation, e is an electron charge, m is a salinity, $\gamma$ is an activity coefficient, $C_+$ is a cation conductivity and $C_-$ is an anion conductivity, and C is a rock conductivity determined substantially according to: $C = C_+ + C_-$.

36. The method of claim 35 wherein said cation conductivity $C_+$ is determined substantially according to:

$$C_+ = S_{xot}^n \varnothing_t^m \left( tC_f + \frac{X}{S_{xot}} \right), \text{ and}$$

said anion conductivity $C_-$ is determined substantially according to:

$$C_- = S_{xot}^n \phi_t^m (1-t) C_f,$$

where t is a cation transference number and $C_f$ is a conductivity of said fluid at said interface.

37. The method of claim 36 wherein said transference number t is determined substantially according to:

$$t = 0.374 - 0.125 \log(\bar{m}) - 1.77e\text{-}3 \log^2(\bar{m}) + 4.047e\text{-}4(T_c^0 - 25) - 8.22e\text{-}7(T_c^0 - 25)^2,$$

and $C_f$ is determined substantially according to:

$$\frac{1}{C_f} = 0.123 + 10^{3.562 - 0.955 \log(\overline{n})}.$$

38. The method of claim 35 wherein said $\gamma$ is determined substantially according to:

$$\log \gamma = \frac{a_1}{\sqrt{\overline{m}}} + a_2 \sqrt{\overline{m}} + a_3 \overline{m} + a_4 \overline{m}^2 + a_5,$$

where said coefficients $a_1$, $a_2$, $a_3$, $a_4$, and $a_5$, are determined substantially according to:

$$a_i = b_i T_c^3 + c_i T_c^2 + d_i T_c + e_i,$$

where i=1, 2, 3, 4, and 5, respectively, $\overline{m}$ is a salinity of solvent determined substantially according to:

$$\overline{m} = \frac{\overline{n}}{58.443(1000 - \overline{n} \, 10^{-3})}, \text{ and}$$

where said coefficients $b_i$, $c_i$, $d_i$, and $e_i$ are about:

| i | $b_i$ | $c_i$ | $d_i$ | $e_i$ |
|---|---|---|---|---|
| 1 | −6.1237e-11 | +3.6490e-08 | −1.2225e-06 | +9.7432e-04, |
| 2 | −3.1529e-08 | +8.7540e-06 | −1.3528e-03 | −2.4460e-01, |
| 3 | +1.5951e-08 | −7.0447e-06 | +1.0840e-03 | +1.0514e-01, |
| 4 | −1.0729e-09 | +5.5435e-07 | −1.0211e-04 | +4.7400e-04, and |
| 5 | +4.1937e-09 | −2.1167e-06 | +1.1317e-04 | −3-6126e-02. |

39. A method for determining a bound fluid volume BFV of a formation with complex lithology that is traversed by a borehole comprising:

receiving NMR data characterizing a flushed zone of said formation, said NMR data at least comprising $P(T_2)$, which is a $T_2$ distribution; and determining a bound fluid volume BFV, said method of determining said BFV comprising summing $BFV_i$ constituents weighted by their respective constituent volumes $V_i$, where i is an index denoting different constituents.

40. The method of claim 39 wherein said determining said BFV is substantially according to:

$$BFV = \frac{\sum_i V_i \int_{T_2 \min}^{T_2 \text{cutoff } i} P(T_2) d T_2}{\sum_i V_i},$$

where $T_2$ min is a minimum $T_2$, and $T_2$ cutoff i is a cutoff $T_2$ of constituent i.

41. The method of claim 40 further comprising determining a permeability k of said formation substantially according to a permeability model.

42. The method of claim 40 further comprising determining a $T_2$cutoff substantially according to:

$$\int_{T_2 \min}^{T_2 \text{cutoff}} P(T_2) d T_2 = BFV,$$

where $T_2$min is a minimum $T_2$ and BFV is a known bound fluid volume for the formation.

43. A method of analyzing the uncertainty of a gas-corrected petrophysical parameter, said method comprising calculating said variance of said parameter substantially according to:

$$\sigma^2(f) \cong \sum_{i=1}^{n} \left( \frac{\partial f}{\partial x_i} \right)_{x_i^*}^2 \sigma^2(x_i),$$

where $f$ is a petrophysical parameter that is a function of n variables $x_n$, $\sigma^2(f)$ is a variance of $f$, and $x_i^*$ is a best estimate for each of said n variables.

44. The method of claim 43 wherein said $f$ is an output selected from the group consisting of gas-corrected total porosity $\phi_t$, a gas volume of the flushed zone $V_{g,xo}$, and a flushed zone gas saturation $S_{g,xo}$, and wherein said calculating uses quantities $N_1$, $N_2$, $\alpha^0$, and D, said quantities being defined substantially according to:

$$N_1 = \phi_{density} - \frac{\phi_{nmr}}{(HI)_f},$$

$$N_2 \equiv 1 - \frac{(HI)_g P_g}{(HI)_f},$$

$$\alpha^0 \equiv \frac{(HI)_g}{(HI)_f}, \text{ and}$$

$$D \equiv 1 - \frac{(HI)_g P_g}{(HI)_f} + \lambda,$$

where $(HI)_g$ is a Hydrogen Index of a gas, $(HI)_f$ is a Hydrogen Index of a fluid, $P_g$ is a gas polarization function, which is defined as $1 - \exp(-WT/T_{l,gas})$, where WT is a wait time for a pulse sequence and $T_{l,gas}$ is a gas longitudinal relaxation time at said condition, $$\lambda = \frac{\rho_f - \rho_g}{\rho_{ma} - \rho_f},$$

where $\rho_f$ is a density of said fluid, $\rho_{ma}$ is a formation matrix density, $\rho_g$ is a density of said gas, $\phi_{nmr}$ is a NMR-derived porosity, and $\phi_{density}$ is a density-derived porosity determined substantially according to:

$$\phi_{density} = \frac{\rho_b - \rho_{ma}}{\rho_f - \rho_{ma}},$$

where $\rho_b$ is a formation bulk density.

45. The method of claim 44 wherein said calculating said variance of said parameter comprises calculating said variance of said $\phi_t$ using:

$$\frac{\partial \phi_t}{\partial \rho_b} = \frac{N_2}{D(\rho_f - \rho_{ma})},$$

$$\frac{\partial \phi_t}{\partial \rho_f} = \frac{N_1 N_2 (\rho_g - \rho_{ma})}{D^2 (\rho_f - \rho_{ma})^2} + \frac{N_2 (\rho_{ma} - \rho_b)}{D(\rho_f - \rho_{ma})^2},$$

$$\frac{\partial \phi_t}{\partial \rho_g} = \frac{N_1 N_2}{D^2 (\rho_{ma} - \rho_f)},$$

$$\frac{\partial \phi_t}{\partial \rho_{ma}} = \frac{N_1 N_2 (\rho_f - \rho_g)}{D^2 (\rho_f - \rho_{ma})^2} + \frac{N_2 (\rho_b - \rho_f)}{D(\rho_f - \rho_{ma})^2},$$

-continued $$\frac{\partial \varnothing_t}{\partial T_{l,g}} = \frac{W\alpha^0 \lambda N_1 e^{-\frac{WT}{T_{l,g}}}}{T_{l,g}^2 D^2},$$

$$\frac{\partial \varnothing_t}{\partial (HI)_f} = \frac{-\lambda \varnothing_{nmr}}{D(HI)_f^2} + \frac{\lambda P_g N_1 \alpha^0}{D^2 (HI)_f},$$

$$\frac{\partial \varnothing_t}{\partial (HI)_g} = \frac{-P_g \lambda N_1}{D^2 (HI)_f}, \text{ and}$$

$$\frac{\partial \varnothing_t}{\partial \varnothing_{nmr}} = \frac{\lambda}{D(HI)_f}.$$

46. The method of claim 44 wherein said calculating said variance of said parameter comprises calculating said variance of said $V_{g,xo}$ using:

$$\frac{\partial V_{g,xo}}{\partial \rho_b} = \frac{1}{D(\rho_f - \rho_{ma})},$$

$$\frac{\partial V_{g,xo}}{\partial \rho_f} = \frac{N_1(\rho_g - \rho_{ma})}{D^2(\rho_f - \rho_{ma})^2} + \frac{(\rho_{ma} - \rho_b)}{D(\rho_f - \rho_{ma})^2},$$

$$\frac{\partial V_{g,xo}}{\partial \rho_g} = \frac{N_1}{D^2(\rho_{ma} - \rho_f)},$$

-continued $$\frac{\partial V_{g,xo}}{\partial \rho_{ma}} = \frac{N_1(\rho_f - \rho_g)}{D^2(\rho_f - \rho_{ma})^2} + \frac{(\rho_b - \rho_f)}{D(\rho_f - \rho_{ma})^2},$$

$$\frac{\partial V_{g,xo}}{\partial T_{l,gas}} = -\frac{W\alpha^0 N_1 e^{-\frac{WT}{T_{l,gas}}}}{T_{l,gas}^2 D^2},$$

$$\frac{\partial V_{g,xo}}{\partial (HI)_f} = \frac{\varnothing_{nmr}}{D(HI)_f^2} - \frac{\alpha^0 P_g N_1}{D^2(HI)_f},$$

$$\frac{\partial V_{g,xo}}{\partial (HI)_g} = \frac{P_g N_1}{D^2(HI)_f}, \text{ and}$$

$$\frac{\partial V_{g,xo}}{\partial \varnothing_{nmr}} = -\frac{1}{D(HI)_f}.$$

47. The method of claim 44 wherein said calculating said variance of said parameter comprises calculating said variance of said $S_{g,xo}$ substantially according to:

$$\sigma^2(S_{g,xo}) = \frac{V_{g,xo}\sigma^2(\varnothing_t)}{\varnothing_t^4} + \frac{\sigma^2(V_{g,xo})}{\varnothing_t^2}.$$

* * * * *